(12) United States Patent
Kim et al.

(10) Patent No.: US 10,130,611 B2
(45) Date of Patent: Nov. 20, 2018

(54) USE OF BENZO-HETEROCYCLE DERIVATIVES FOR PREVENTING AND TREATING CANCER OR FOR INHIBITING CANCER METASTASIS

(75) Inventors: Sunghoon Kim, Seoul (KR); Jin Woo Choi, Seoul (KR); Jin Young Lee, Seoul (KR); Dae Gyu Kim, Seoul (KR); Gyoon Hee Han, Hwaseong-si (KR); Jee Sun Yang, Seoul (KR); Chul Ho Lee, Seoul (KR)

(73) Assignee: MEDICINAL BIOCONVERGENCE RESEARCH CENTER (KR)

( * ) Notice: Subject to any disclaimer, the term of this patent is extended or adjusted under 35 U.S.C. 154(b) by 935 days.

(21) Appl. No.: 13/465,709

(22) Filed: May 7, 2012

(65) Prior Publication Data
US 2012/0283300 A1 Nov. 8, 2012

Related U.S. Application Data

(63) Continuation of application No. PCT/KR2010/007806, filed on Nov. 5, 2010.

(30) Foreign Application Priority Data

Nov. 5, 2009 (KR) .................. 10-2009-0106350

(51) Int. Cl.
*A61K 31/4184* (2006.01)
*A61K 31/423* (2006.01)
*A61K 31/428* (2006.01)

(52) U.S. Cl.
CPC ........ *A61K 31/4184* (2013.01); *A61K 31/423* (2013.01); *A61K 31/428* (2013.01)

(58) Field of Classification Search
None
See application file for complete search history.

(56) References Cited

U.S. PATENT DOCUMENTS

2004/0198768 A1* 10/2004 Park Choo ........... A61K 31/423
514/301

FOREIGN PATENT DOCUMENTS

| EP | 1 724 263 | 11/2006 |
|----|-----------|---------|
| WO | 2008/056150 | 5/2008 |
| WO | 2008/151437 | 12/2008 |

OTHER PUBLICATIONS

Calabresi P and Chabner BA, "Section IX Chemotherapy of Neoplastic Diseases—Introduction," Goodman & Gilman's The Pharmacological Basis of Therapeutics 10th ed., 2001, Hardman JG, Limbird LE, and Gilman AG, Eds, McGraw-Hill, New York 2001, 1381-1388 (pp. 1381, 1383-1385, and 1388 provided).*

(Continued)

*Primary Examiner* — Marcos L Sznaidman
*Assistant Examiner* — Rayna Rodriguez
(74) *Attorney, Agent, or Firm* — Levenfeld Pearlstein, LLC

(57) ABSTRACT

This application relates to a novel benzo-heterocycle derivative and more particularly, it relates a composition for preventing and treating cancer or for inhibiting metastasis comprising benzo-heterocycle derivative or pharmaceutically acceptable salts thereof as an active ingredient. The present inventors confirmed that KRS has an effect on cancer metastasis by facilitating cancer (or tumor) cell migration through interaction with 67LR, and also found that a substance inhibiting the interaction between KRS and 67LR can prevent and treat cancer by inhibiting cancer cell metastasis. Accordingly, the composition of the present invention can inhibit cancer metastasis, and thus provide a novel means for prevention and treatment of cancer.

1 Claim, 25 Drawing Sheets

(56) References Cited

OTHER PUBLICATIONS

Matsuyama M, Yoshimura R. The target of arachidonic acid pathway is a new anticancer strategy for human prostate cancer. Biologics. Dec. 2008;2(4):725-32.*

Steele VE, Holmes CA, Hawk ET, Kopelovich L, Lubet RA, Crowell JA, Sigman CC, Kelloff GJ. Lipoxygenase inhibitors as potential cancer chemopreventives. Cancer Epidemiol Biomarkers Prev. May 1999;8(5):467-83.*

Yoshimura R, Matsuyama M, Tsuchida K, Kawahito Y, Sano H, Nakatani T. Expression of lipoxygenase in human bladder carcinoma and growth inhibition by its inhibitors. J Urol. Nov. 2003;170(5):1994-9.*

Hande (Update on Cancer Therapeutics, 2008; 3:13-26).*

Wilhem et al (Nature Reviews: Drug Discover, 2006; 5(10): 835-44).*

Carpenter, R.D., et al., "Selectively Targeting T- and B-Cell Lymphomas: A Benzothiazole Antagonist of a1b1 Integrin", J. Med. Chem., 52 (2009) 14-19.

Choi, S.J. et al., "Solid phase combinatorial synthesis of benzothiazoles and evaluation of topoisomerase II inhibitory activity", Bioorganic & Medicinal Chemistry, 14 (2006) 1229-1235.

Lage, H., "High aantineoplastic activity of new heterocyclic compounds in cancer cells with resistance against classical DNA topoisomerase H-targeting drugs", Int. J. Cancer, 119 (2006) 213-220.

Manjula, S.N., et al., "Synthesis and antitumor activity of optically active thiourea and their 2-aminobenzothiazole derivatives: A novel class of anticancer agents", European Journal of Medicinal Chemistry, 44 (2009) 2923-2929.

Popov, D., "Antitumor screening studies of oxazole derivatives", Problemi na Onkologiyata (1980), 8, 59-62.

Song, E.Y. et al., "Synthesis of amide and urea derivatives of benzothiazole as Raf-1 inhibitor", European Journal of Medicinal Chemistry, 43 (2008) 1519-1524.

Campo et al., "Detection of laminin receptor mRNA in human cancer cell lines and colorectal tissues by in situ hybridization." Am J Pathol. Nov. 1992;141(5): 1073-83.

Castronovo et al., "Laminin receptor complementary DNA-deduced synthetic peptide inhibits cancer cell attachment to endothelium." Cancer Res.. Oct. 15, 1991;51(20):5672-8.

Chen et al., "Down-regulation of 67LR reduces the migratory activity of human glioma cells in vitro." Brain Res Bull. Aug. 14, 2009;79(6):402-8.

Ménard et al., "The 67 kDa laminin receptor as a prognostic factor in human cancer." Breast Cancer Res Treat. 1998;52(1-3):137-45.

Nelson et al., "The 67 kDa laminin receptor: structure, function and role in disease." Biosci. Rep. The Authors Journal compilation vol. 28(1); pp. 33-48. 2008 Biochemical Society.

van den Brule FA et al., "Expression of the 67-kD laminin receptor, galectin-1, and galectin-3 in advanced human uterine adenocarcinoma." Hum Pathol. Nov. 1996; 27(11):1185-91.

* cited by examiner

USE OF BENZO-HETEROCYCLE DERIVATIVES FOR PREVENTING AND TREATING CANCER OR FOR INHIBITING CANCER METASTASIS

CROSS-REFERENCE TO RELATED APPLICATIONS

This is a continuation application of PCT/KR2010/007806 filed Nov. 5, 2010, which claims the priority to Korean Application No. 10-2009-0106350 filed Nov. 5, 2009, which applications are incorporated herein by reference in their entirety.

TECHNICAL FIELD

This application claims priority from and the benefit of Korean Patent Application No. 10-2009-0106350, filed on Nov. 5, 2009, which is hereby incorporated by reference for all purposes as if fully set forth herein.

BACKGROUND ART

This application relates to a novel benzo-heterocycle derivative and more particularly, it relates a composition for preventing and treating cancer or for inhibiting metastasis comprising benzo-heterocycle derivative or pharmaceutically acceptable salts thereof as an active ingredient.

A Cancer (or tumor) is developed by uncontrollable disordered abnormal cell proliferation. Especially, if this tumor shows a destructive growth, invasiveness and metastasis, it is regarded as a malignant cancer. Invasiveness is a character to infiltrate or destroy surrounding tissues, and in particular, a basal layer forming a boundary of tissues is destroyed by the character, resulting in the local spread and sometimes inflow of a tumor through circulatory system. Metastasis means the spread of tumor cells from the original birthplace to other areas through lymphatic or blood vessels. In a broad sense, metastasis also means the direct extension of tumor cells through serous body cavity or other space.

These days, surgical operation, radiotherapy and chemotherapy are widely used for the treatment of cancer singly or jointly. The surgical operation is a way to remove diseased tissues. Thus, tumors in specific regions such as breast, colon and skin can be effectively removed by the surgical operation. However, a tumor in vertebra or dispersive tumor like leukemia cannot be properly treated by the surgical operation.

Chemotherapy blocks cell replication or metabolism, and has been used for the treatment of breast cancer, lung cancer and testicular cancer. Though, patients with cancers who have been treated by chemotherapy have seriously suffered from the side effects of systemic chemotherapy. Motion sickness and vomiting are common but serious examples of all. The side effects of chemotherapy can even affect the life of a patient since they might drop the adaptability of a patient rapidly. Besides, DLT (Dose Limiting Toxicity) is also one of major side effects of chemotherapy, which draws a careful attention in the administration of a medicine. Mucositis is an example of DLT against anticancer agents such as 5-fluorouracil which is an antimetabolic cytotoxic agent, and methotrexate, and anticancer antibiotics like doxorubicin. If a patient suffers seriously from such side effects of chemotherapy, he or she should be hospitalized and given an anodyne for reducing pain. So, side effects of chemotherapy and radiotherapy are the biggest problem for the treatment of cancer patients.

Metastatic spread is a critical determinant for the lethality of cancer. 67 kDa laminin receptor (67LR) is non-integrin type receptor embedded in plasma membrane and associated with cancer invasion and metastasis (Nelson, J. et al. The 67 kDa laminin receptor: structure, function and role in disease. Biosci. Rep. 28, 33-48 (2008)). 67LR is generated from dimerization of its 37 kDa precursor (37LRP) although molecular detail of this conversion process is not understood. 37LRP is identical to ribosomal subunit p40 that is involved in the formation of polysome (Auth, D. & Brawerman, G. A 33-kDa polypeptide with homology to the laminin receptor: component of translation machinery. Proc. Natl. Acad. Sci. USA 89, 4368-4372 (1992)). 67LR is often observed at high level in a variety of cancers (Nelson, J. et al. The 67 kDa laminin receptor: structure, function and role in disease. Biosci. Rep. 28, 33-48 (2008); Menard, S., Castronovo, V., Tagliabue, E. & Sobel, M. E. New insights into the metastasis-associated 67 kD laminin receptor. J. Cell. Biochem. 67, 155-165 (1997)). However, the regulator and molecular mechanism for the membrane residency of 67LR have not been determined yet. In this work, the present inventors found that lysyl-tRNA synthetase (KRS) enhances cell migration and cancer metastasis by stabilizing 67LR at plasma membrane.

KRS belongs to aminoacyl-tRNA synthetases (ARSs) that ligate their cognate amino acids and tRNAs for protein synthesis. These ancient enzymes show pleiotropic functions in addition to their catalytic activities (Park, S. G., Ewalt, K. L. & Kim, S. Functional expansion of aminoacyl-tRNA synthetases and their interacting factors: new perspectives on housekeepers. Trends Biochem. Sci. 30, 569-574 (2005)). Besides, several mammalian ARSs including KRS form a macromolecular complex (Lee, S. W., Cho, B. H., Park, S. G. & Kim, S. Aminoacyl-tRNA synthetase complexes: beyond translation. J. Cell. Sci. 117, 3725-3734 (2004); Han, J. M., Kim, J. Y. & Kim, S. Molecular network and functional implications of macromolecular tRNA synthetase complex. Biochem. Biophys. Res. Commun. 303, 985-993 (2003)), which serve as molecular reservoir (Ray, P. S., Arif, A. & Fox, P. Macromolecular complexes as depots for releasable regulatory proteins. Trends Biochem. Sci. 32, 158-164 (2007). to control multiple functions of the component proteins. Human KRS contains unique N-terminal extension involved in the interactions with RNA and other proteins ( ).

SUMMARY OF THE DISCLOSURE

Accordingly, the present inventors conducted research on the functional diversity of a human lysyl-t-RNA synthetase (KRS), and found that 37LRP/p40 is one of proteins capable of binding to human KRS. Also, they found that KRS facilitates cell migration and cancer metastasis by stabilizing a laminin receptor (67LR) formed by dimerization of 37LRP, on a plasma membrane, in other words, KRS has an effect on cancer metastasis or cancer cell migration through a laminin receptor on a plasma membrane. Since a substance inhibiting the interaction between KRS and 67LR has a cancer prevention/treatment effect through inhibition of cancer metastasis, we found a novel use of a benzo-hetero cycle derivative inhibiting the interaction, and based on this finding, completed this invention.

Accordingly, on object of the present invention is to provide a use of a benzo-hetero cycle derivative that prevents and treats cancer by inhibiting cancer metastasis through inhibition of the interaction between KRS and 67LR.

To achieve the above object, the present invention provides a pharmaceutical composition for preventing and treating cancer comprising benzo-heterocycle derivative or pharmaceutically acceptable salts thereof.

To achieve another object, the present invention provides a pharmaceutical composition for inhibiting metastasis comprising benzo-heterocycle derivative or pharmaceutically acceptable salts thereof.

To achieve still another object, the present invention provides a use of benzo-heterocycle derivative or pharmaceutically acceptable salts thereof for preparing an agent for preventing and treating cancer.

To achieve still another object, the present invention provides a use of benzo-heterocycle derivative or pharmaceutically acceptable salts thereof for preparing an agent for inhibiting metastasis.

To achieve still another object, the present invention provides a method for preventing and treating cancer comprising administering to a subject in need thereof an effective amount of benzo-heterocycle derivative or pharmaceutically acceptable salts thereof.

To achieve still another object, the present invention provides a method for inhibiting metastasis comprising administering to a subject in need thereof an effective amount of benzo-heterocycle derivative or pharmaceutically acceptable salts thereof.

DETAILED DESCRIPTION OF THE DISCLOSURE

Figure 1:
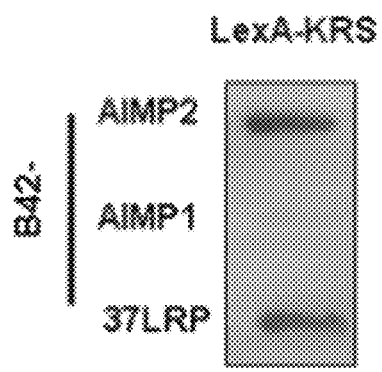
FIG. 1 shows the interaction between human KRS and 37LRP/p40, which was determined by a yeast two-hybrid assay.

Hereafter, the present invention will be described in detail.

The present inventors firstly confirmed that KRS has an effect on cancer metastasis or cancer cell migration. In other words, in the present invention, it was confirmed that KRS has an effect on cancer metastasis or cancer cell migration through a laminin receptor (67LR) on a plasma membrane. Also, they firstly confirmed that a substance inhibiting the interaction between KRS and 67LR inhibits cancer metastasis, and thus can be used for the prevention and treatment of cancer, and then, selected a benzo-hetero cycle derivative compound by screening a library of compounds.

The term "KRS", "KRS protein" or "KRS polypeptide" refers to a polypeptide known as lysyl tRNA synthetase. The said KRS polypeptide may be a polypeptide well known in the art but, preferably it may a polypeptide having an amino acid sequence of GenBank Accession No: NP_005539. And the KRS of the present invention includes functional equivalents thereof.

The term "functional equivalents" refers to polypeptide comprising the amino acid sequence having at least 70% amino acid sequence homology (i.e., identity) with the amino acid sequence of GenBank Accession No: NP_005539, preferably at least 80%, and more preferably at least 90%, for example, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100% amino acid sequence homology, that exhibit substantially identical physiological activity to the polypeptide having the amino acid sequence of GenBank Accession No: NP_005539. The "substantially identical physiological activity" means interaction with laminin receptor of plasma membrane and regulation of tumor metastasis or tumor cell migration.

The "laminin receptor" or "laminin receptor of 67 kDa (67LR)" is plasma membrane-embedded, non-integrin receptor and for example, it may have a nucleotide sequence or amino acid sequence any one disclosed in Genbank Accession No. NM_002295, S37431, AF284768, S37431, AF284768, J03799, XP_370865, XP 001083023. In addition, the laminin receptor of the present invention may comprise functional equivalents thereof.

In the present invention, for the inhibition of the interaction between KRS and 67LR, a protein-protein interaction detecting method known in the art may be used, for example, various methods known in the art, such as in vitro protein-protein binding assays (in vitro pull-down assays), EMSA (electrophoretic mobility shift assays), immunoassays for protein binding, functional assays (phosphorylation assays, etc.), assays of non-immune immunoprecipitations, immunoprecipitation western blotting assays, immuno-co-localization assays, cross-linking, affinity chromatography, immunoprecipitation (IP), yeast two-hybrid (Y2H), fluorescence resonance energy transfer (FRET), bimolecular fluorescence complementation (Bi—FC), and the like, may be used.

For the screening of the compound of the present invention, for example, a yeast-2 hybrid assay may be carried out by using yeast expressing KRS and 67LR, or parts or homologues of the proteins, fused with the DNA-binding domain of bacteria repressor LexA or yeast GAL4 and the transactivation domain of yeast GAL4 protein, respectively (KIM, M. J. et al., *Nat. Gent.*, 34:330-336, 2003). The interaction between KRS and 67LR reconstructs a transactivator inducing the expression of a reporter gene under the control by a promoter having a regulatory sequence binding to the DNA-binding domain of LexA protein or GAL4.

As described above, the reporter gene may be any gene known in the art encoding a detectable polypeptide. For example, CAT (chloramphenicol acetyltransferase), luciferase, beta-galactosidase, beta-glucositase, alkaline phosphatase, GFP (green fluorescent protein), etc. may be used. If the interaction between KRS and 67LR, or parts or homologues of the proteins is facilitated or enhanced by a test agent, the expression of the reporter gene increases more than that under a normal condition. On the other hand, if the interaction is inhibited or reduced by a test agent, the reporter gene is not expressed or expressed less than that under a normal condition.

Also, a reporter gene encoding a protein which enables growth of yeast (i.e., if the reporter gene is not expressed, the growth of yeast is inhibited) may be selected. For example, auxotropic genes encoding enzymes involved in biosynthesis for obtaining amino acids or nitrogen bases (e.g., yeast genes such as ADE3, HIS3, etc. or similar genes from other species) may be used. If the interaction of AIMP2 and p53, or parts or homologues of the proteins, expressed in this system, is inhibited or reduced by a test agent, the reporter gene is not expressed or expressed less. Accordingly, under such a condition, the growth of yeast is stopped or retarded. Such an effect by the expression of the reporter gene may be observed with the naked eye or by using a device (e.g., a microscope).

In the present invention, a compound library was screened by the screening method. Then, the inventors determined that derivative compounds of benzoxazole, benzothiazole, and benzopyrrole have a cancer prevention/treatment effect by inhibiting cancer metastasis through inhibition of the interaction between KRS and 67LR.

In accordance with an aspect of the present invention, there is provided a pharmaceutical composition for preventing and treating cancer, the pharmaceutical composition comprising a benzo-heterocycle derivative represented by Formula 1 below or its pharmaceutically acceptable salt, as an active ingredient.

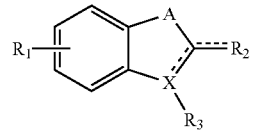

[Formula 1]

Wherein, ~~~~~ represents a double bond or single bond (in which as required atoms are acceptable);

A is selected from the group comprising O, NH and S;

X represents C or N;

R₁ is selected from the group comprising hydrogen, alkyl unsubstituted or substituted with halogen, alkoxy, halogen, nitro and amine;

R₂ is selected from the group comprising hydrogen, arylalkyl,

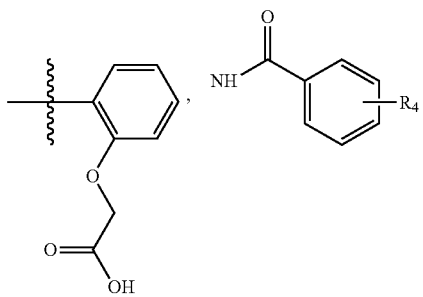

and —NH—R₅,

R₄ represents hydrogen or alkyl unsubstituted or substituted with halogen;

R₅ represents aryl unsubstituted or substituted with halogen, or arylalkyl unsubstituted or substituted with halogen; and R₃ is selected from the group comprising hydrogen,

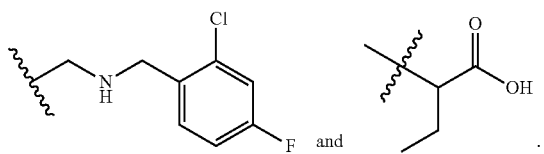

"alkyl" indicates a straight-chain or branched aliphatic hydrocarbon group having about 1 to 20 carbon atoms in the chain. Preferably, an alkyl group includes about 1 to 12 carbon atoms in the chain. More preferably, an alkyl group includes about 1, 2, 3, 4, 5 or 6 carbon atoms in the chain. A branched group indicates that at least one lower alkyl group, for example, methyl, ethyl or propyl, is attached to a linear alkyl chain. The term "lower alkyl" indicates a straight-chain or branched group having about 1 to 6 carbon atoms. "alkyl" may be unsubstituted or optionally substituted with at least one same or different substituent, in which each substituent may be halogen, alkyl, aryl, cycloalkyl, cyano, hydroxy, alkoxy, alkylthio, amino, carboxy or the like. Preferably, alkyl may be methyl, ethyl, butyl or isobutyl.

"Alkoxy" indicates an alkyl-O-group in which the alkyl group is as previously described. Appropriate examples of the alkoxy group include methoxy, ethoxy, n-propoxy, iso-propoxy and n-butoxy. Alkoxy is bonded to a parental residue through oxygen. Preferably, alkoxy may be methoxy or ethoxy.

"aryl" means an aromatic hydrocarbon ring system, and its examples include phenyl, indenyl, indanyl, naphthyl, fluorenyl and the like.

Also, "halogen" may include a fluorine atom, a chlorine atom, a bromine atom, or an iodine atom, and preferably may be a fluorine atom, a chlorine atom, or a bromine atom.

"alkyl substituted with halogen" means an alkyl group substituted with 1 to 3 halogen atom(s), for example, may be fluoromethyl, chloromethyl, difluoromethyl, dichloromethyl, dibromomethyl, trifluoromethyl, trichloromethyl, fluoroethyl, chloroethyl, trifluoroethyl, trichloroethyl, fluoropropyl, fluorobutyl, fluorohexyl or the like. Preferably, it may be (C1-C6)alkyl substituted with halogen, and more preferably it may be (C1-C6)alkyl substituted with chlorine or fluorine. Most preferably, it may be trifluoromethyl.

"aryl substituted with halogen" means an aryl group substituted with 1 to 3 halogen atom(s), for example, may be fluorophenyl, difluorophenyl, trifluorophenyl, chlorophenyl, dichlorophenyl, trichlorophenyl, bromophenyl, dibromophenyl, tribromophenyl, difluorobenzyl, dichlorobenzyl, dibromobenzyl or the like. Preferably, it may be chlorophenyl.

"aryl substituted with alkyl" or "arylalkyl" means an aryl group substituted with 1 to 3 alkyl substituents, for example, may be benzyl, ethylphenyl, propylphenyl, dimethylphenyl, diethylphenyl, trimethylphenyl, triethylphenyl or the like. Preferably it may be benzyl.

Preferably, in the compound of the present invention represented by Formula 1, R₁ may represent hydrogen, methyl, trifluoromethyl, methoxy, ethoxy, chloro, nitro or amine, R₂ may represent hydrogen, 2,4,6-trimethylphenyl (2,4,6-Trimethyl-phenyl), 2,6-dimethoxyphenyl (2,6-Dimethoxy-phenyl),

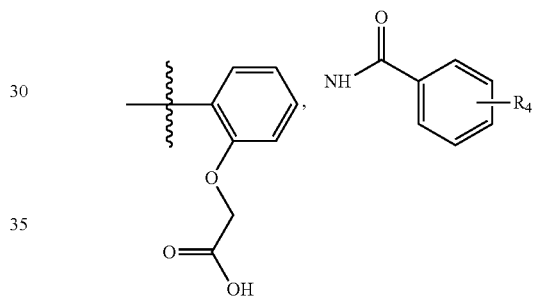

or —NH—R₅, R₄ may represent hydrogen or trifluoromethyl, R₅ may represent phenyl (Phenyl), 4-ethyl-phenyl (4-Ethyl-phenyl), 3,4-dichloro-phenyl (3,4-Dichloro-phenyl), or 4-phenylazo-phenyl (4-Phenylazo-phenyl). Also, R₃ may represent hydrogen,

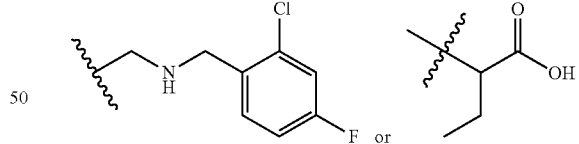

More specifically, the compound which was determined to show an anticancer effect by inhibiting the interaction between KRS and 67LR, and its source are noted in Table 1 below.

TABLE 1

| No. of formula | name | Reference or Registration No. |
|---|---|---|
| 2 | N-(6-Methoxy-benzooxazol-2-yl)-benzamide | Pandeya, Surendra N.; Shankar, Vinod. Synthesis of benzothiazole derivatives and their insecticidal and larvicidal activities. Indian Drugs (1985), 23(3), 146-51. CODEN: INDRBA ISSN: 0019-462X. |

TABLE 1-continued

| No. of formula | name | Reference or Registration No. |
|---|---|---|
| 3 | N-(5-Methoxy-benzooxazol-2-yl)-benzamide | CAN 104: 124989 AN 1986: 124989 CAPLUS Pandeya, Surendra N.; Shankar, Vinod. Synthesis of benzothiazole derivatives and their insecticidal and larvicidal activities. Indian Drugs (1985), 23(3), 146-51. CODEN: INDRBA ISSN: 0019-462X. CAN 104: 124989 AN 1986: 124990 CAPLUS |
| 4 | (5-Chloro-benzooxazol-2-yl)-phenyl-amide | Yoon, Ju Hee; Song, Hyunmin; Kim, Sang Wong; Han, Gyoonhee; Choo, Hea-Young Park. A facile synthesis of 2-aminothiazolo[5,4-b]pyridines and 2-aminobenzoxazoles via cyclization of thioureas. Hetercycles (2005), 65(11), 2729-2740. CODEN: HTCYAM ISSN: 0385-5414. CAN 144: 88204 AN 2005: 1225849 CAPLUS |
| 5 | (5-Chloro-benzooxazol-2-yl)-(4-ethyl-phenyl)-amide | Yoon, Ju Hee; Song, Hyunmin; Kim, Sang Wong; Han, Gyoonhee; Choo, Hea-Young Park. A facile synthesis of 2-aminothiazolo[5,4-b]pyridines and 2-aminobenzoxazoles via cyclization of thioureas. Hetercycles (2005), 65(11), 2729-2740. CODEN: HTCYAM ISSN: 0385-5414. CAN 144: 88204 AN 2005: 1225849 CAPLUS |
| 6 | (5-Chloro-benzooxazol-2-yl)-(3,4-dichloro-phenyl)-amide | Yoon, Ju Hee; Song, Hyunmin; Kim, Sang Wong; Han, Gyoonhee; Choo, Hea-Young Park. A facile synthesis of 2-aminothiazolo[5,4-b]pyridines and 2-aminobenzoxazoles via cyclization of thioureas. Hetercycles (2005), 65(11), 2729-2740. CODEN: HTCYAM ISSN: 0385-5414. CAN 144: 88204 AN 2005: 1225849 CAPLUS |
| 7 | (5-Nitro-benzooxazol-2-yl)-(4-phenylazo-phenyl)-amide | Park, Choo Hea Young; Chang, Hyeun Wook; Yoon, Ju Hee; Ju, Hye Kyung. Method for inhibiting 5-lipoxygenase using a benzoxazole derivative or an analogue thereof. U.S. patent application Publ. (2004), 11 pp. CODEN: USXXCO US 2004198768 A1 20041007 CAN 141: 332184 AN 2004: 825136 CAPLUS |
| 8 | N-Benzooxazol-2-yl-benzamide | Kumari, T. Aruna; Rao, P. Jayaprasad. A facile synthesis of 7-substituted 3-(aroylimino)benzoxazolo[3,2-b][1,2,4]thiadiazolines. Indian Journal of Heterocyclic Chemistry (2001), 11(1), 9-14. CODEN: IJCHEI ISSN: 0971-1627. CAN 136: 232245 AN 2001: 808784 CAPLUS |
| 9 | N-(5-Nitro-benzooxazol-2-yl)-benzamide | Pandeya, Surendra N.; Shankar, Vinod. Synthesis of benzothiazole derivatives and their insecticidal and larvicidal activities. Indian Drugs (1985), 23(3), 146-51. CODEN: INDRBA ISSN: 0019-462X. CAN 104: 124989 AN 1986: 124989 CAPLUS |
| 10 | N-(5-Methoxy-benzooxazol-2-yl)-benzamide | Pandeya, Surendra N.; Shankar, Vinod. Synthesis of benzothiazole derivatives and their insecticidal and larvicidal activities. Indian Drugs (1985), 23(3), 146-51. CODEN: INDRBA ISSN: 0019-462X. CAN 104: 124989 AN 1986: 124989 CAPLUS |
| 11 | N-(5-Methyl-benzooxazol-2-yl)-benzamide | Pandeya, Surendra N.; Shankar, Vinod. Synthesis of benzothiazole derivatives and their insecticidal and larvicidal activities. Indian Drugs (1985), 23(3), 146-51. CODEN: INDRBA ISSN: 0019-462X. CAN 104: 124989 AN 1986: 124989 CAPLUS |
| 12 | N-(6-Nitro-benzothiazol-2-yl)-4-trifluoromethyl-benzamide | Song, Eun Young; Kaur, Navneet; Park, Mi-Young; Jin, Yinglan; Lee, Kyeong; Kim, Guncheol; Lee, Ki Youn; Yang, Jee Sun; Shin, Jae Hong; Nam, Ky-Youb; No, Kyoung Tai; Han, Gyoonhee. Synthesis of amide and urea derivatives of benzothiazole as Raf-1 inhibitor. European Journal of Medicinal Chemistry (2008), 43(7), 1519-1524. CODEN: EJMCA5 ISSN: 0223-5234. CAN 149: 267949 AN 2008: 798757 CAPLUS |
| 13 | [2-(5-Methyl-benzooxazol-2-yl)-phenoxy]-acetic acid | 1004065-64-8 |
| 14 | 2-(2,4,6-Trimethyl-phenyl)-benzooxazol-5-ylamine | 1019441-52-1 |
| 15 | 2-[2-(4-Methyl-benzoylimino)-benzothiazol-3-yl]-butyric acid | 1043705-09-4 |
| 16 | 2-(2,6-Dimethoxy-phenyl)-benzothiazole | Choi, Suk-June; Park, Hyen Joo; Lee, Sang Kook; Kim, Sang Woong; Han, Gyoonhee; Choo, Hea-Young Park. Solid phase combinatorial synthesis of benzothiazoles and evaluation of topoisomerase II inhibitory activity. Bioorganic & Medicinal Chemistry (2006), 14(4), 1229-1235. CODEN: BMECEP ISSN: 0968-0896. CAN 144: 163516 AN 2006: 19703 CAPLUS |
| 17 | (2-Chloro-4-fluoro-benzyl)-(5-fluoro-1H-indol-3-ylmethyl)-amine | 1048142-01-3 |

[Formula 2]

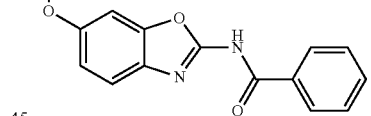

[Formula 3]

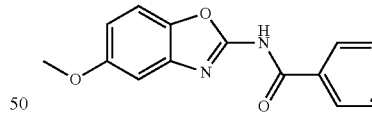

[Formula 4]

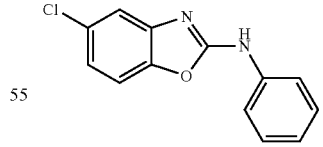

[Formula 5]

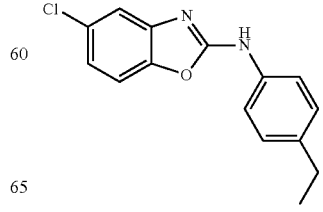

TABLE 1-continued

| No. of formula | name | Reference or Registration No. |
|---|---|---|
| [Formula 6] | | |
| [Formula 7] | | |
| [Formula 8] | | |
| [Formula 9] | | |
| [Formula 10] | | |
| [Formula 11] | | |
| [Formula 12] | | |
| [Formula 13] | | |
| [Formula 14] | | |
| [Formula 15] | | |
| [Formula 16] | | |
| [Formula 17] | | |

More particularly, the present invention provides a pharmaceutical composition for preventing and treating cancer comprising N-(6-Methoxy-benzooxazol-2-yl)-benzamide of formula 2, N-(5-Methoxy-benzooxazol-2-yl)-benzamide of formula 3, (5-Chloro-benzooxazol-2-yl)-phenyl-amine of formula 4, (5-Chloro-benzooxazol-2-yl)-(4-ethyl-phenyl)-amine) of formula 5, (5-Chloro-benzooxazol-2-yl)-(3,4-dichloro-phenyl)-amine) of formula 6, (5-Nitro-benzooxazol-2-yl)-(4-phenylazo-phenyl)-amine) of formula 7, N-Benzooxazol-2-yl-benzamide of formula 8, N-(5-Nitro-benzooxazol-2-yl)-benzamide of formula 9, N-(5-Methoxy-benzooxazol-2-yl)-benzamide of formula 10, N-(5-Methyl-benzooxazol-2-yl)-benzamide of formula 11, N-(6-Nitro-benzothiazol-2-yl)-4-trifluoromethyl-benzamide of formula 12, [2-(5-Methyl-benzooxazol-2-yl)-phenoxy]-acetic acid of formula 13, (2-(2,4,6-Trimethyl-phenyl)-benzooxazol-5-ylamine of formula 14, 2-[2-(4-Methyl-benzoylimino)-benzothiazol-3-yl]-butyric acid of formula 15, (2-(2,6-Dimethoxy-phenyl)-benzothiazole of formula 16 and (2-Chloro-4-fluoro-benzyl)-(5-fluoro-1H-indol-3-ylmethyl)-amine of formula 17 or pharmaceutically acceptable salts thereof as an active ingredient.

The screened compound by the screening method of the present invention may be applied to various cancers since it inhibits metastasis of primary tumor cells. The cancers include, but are not limited to, colon cancer, lung cancer, liver cancer, stomach cancer, esophagus cancer, pancreatic cancer, gall bladder cancer, kidney cancer, prostate cancer, testis cancer, cervical cancer, endometrial carcinoma, choriocarcinoma, ovarian cancer, breast cancer, thyroid cancer, brain tumor, head or neck cancer, malignant melanoma, lymphoma and aplastic anemia. Moreover, the prevention and treatment of cancer are performed by inhibiting metastasis of tumor cell with interaction of KRS and 67LR of the present invention which reduce tumor cell migration and metastasis.

The composition of the present invention may be used as it is or in the form of a pharmaceutically acceptable salt. The "pharmaceutically acceptable" means that the components present in the composition are physiologically acceptable and usually do not invoke allergic or similar reactions when administered to humans. Specifically, the salt may be an acid addition salt formed from a pharmaceutically acceptable free acid. The free acid may be an organic or inorganic acid. The organic acid includes but is not limited to citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, glutamic acid and aspartic acid. And, the inorganic acid includes but is not limited to hydrochloric acid, bromic acid, sulfuric acid and phosphoric acid.

When the compound or a composition comprising the compound of the present invention is clinically administered, the composition of the present invention may be formulated into a unit dosage form of pharmaceutical formulation appropriate for oral or parenteral administration. When the composition is formulated into a general medicine form, a conventionally used diluent or excipient, such as a filler, an extender, a binder, a wetting agent, a disintegrating agent, a surfactant, etc. is used for the preparation. Examples of a solid preparation for oral administration may include tablets, pills, powders, granules, capsules and the like, and such a solid preparation is prepared by mixing the compound of the present invention with at least one excipient, for example, starch, calcium carbonate, sucrose, lactose, gelatin, or the like. Also, besides a simple excipient, lubricants such as magnesium stearate talc are used. Examples of a liquid preparation for oral administration may include a suspension, a liquid for internal use, an emulsion, a syrup, and the like, and the liquid preparation may include not only a generally used simple diluent, such as water, and liquid paraffin, but also various excipients, for example, a wetting agent, a sweetening agent, an aromatic agent, a preservative, etc. Examples of a preparation for parenteral administration include a sterilized aqueous solution, a nonaqueous solvent, a suspension, an emulsion, a freeze-drying agent, an ointment, and a cream. As a nonaqueous solvent, or a suspension solvent, propylene glycol, polyethylene glycol, vegetable oil (such as olive oil), injectable ester (such as ethyloleate), or the like may be used.

Also, the compound of the present invention or the composition comprising the compound may be parenterally administered, and the parenteral administration is carried out by subcutaneous injection, intravenous injection, intramuscular injection or infrasternal injection. For formulation into a form for parenteral administration, the compound of the present invention represented by Formulas 1 to 17 is prepared into a solution or a suspension liquid in mixture with a stabilizing agent or a buffer in water, and then is formulated into a unit dosage form of an ample or a vial. The dosage units can contain, for example, 1, 2, 3 or 4 times of an individual dose or ½, ⅓ or ¼ times of an individual dose. The individual dose preferably contains the amount of an effective drug which is administered in one dosage and which generally corresponds to a whole, a half, a third or a quarter of a daily dose. The dosage may vary according to the body weight, age, sex, health condition, diet, administration duration, administration method, excretion rate, medicine-mixtures and disease severity for a certain patient.

These formulations are disclosed in general reference for pharmaceutical chemistry (*Remington's Pharmaceutical Science,* 15th Edition, 1975, Mack Publishing Company, Easton, Pa.).

In addition, as foregoing, the composition of the present invention inhibits interaction of KRS and 67LR and inhibits migration or metastasis of primary tumor cells or cancer cells. Therefore, the present invention provides a pharmaceutical composition for inhibiting metastasis comprising the composition of the present invention or pharmaceutically acceptable salts thereof. The composition may one of the compositions represented by formula 1 to 17.

Meanwhile, a pharmaceutical composition of the present invention may comprise 0.001 to 99.999 weight % of the composition represented by formula 1 to 17 and the rest may be a pharmaceutically acceptable carrier.

Also, a pharmaceutical composition of the present invention may be administered together with a well known composition having effects on preventing and treating cancer or inhibiting metastasis.

The present invention provides a use of benzo-heterocycle derivative represented by formula 1 or pharmaceutically acceptable salts thereof for preparing a reagent for preventing and treating cancer.

Also, the present invention provides a use of benzo-heterocycle derivative represented by formula 1 or pharmaceutically acceptable salts thereof for preparing a reagent for inhibiting metastasis.

Also, the present invention provides a method for preventing and treating cancer comprising administering to a subject in need thereof an effective amount of benzo-heterocycle derivative represented by formula 1 or pharmaceutically acceptable salts thereof.

Also, the present invention provides a method for inhibiting metastasis comprising administering to a subject in need thereof an effective amount of benzo-heterocycle derivative represented by formula 1 or pharmaceutically acceptable salts thereof.

The benzo-heterocycle derivative may one of the compounds represented by formula 1 to 17.

The benzo-heterocycle derivative of the present invention or pharmaceutically acceptable salts thereof may be administered through various route comprising oral, intracutaneous, subcutaneous, intravenous or intramuscular administration. The "acceptable amount" refers the mount showing effects on preventing and treating cancer or inhibiting metastasis when it is administered to a patient and the "subject" refers to animals, particularly, mammals comprising human and the subject may be cells, tissues or organs originated from the animals. The subject may be patient in need of treatment.

The benzoheterocycle derivative of the present invention or its pharmaceutically acceptable salt may be administered as it is, or may be prepared into various formulations as described above for administration. Preferably, it may be administered until a required effect, that is, a cancer prevention/treatment effect or a cancer metastasis inhibiting effect, is obtained. The compound of the present invention or its pharmaceutically acceptable salt may be administered by various routes according to a method known in the art. In other words, it may be administered orally or parenterally, for example, buccally, intramuscularly, intravenously, intracutaneously, intraarterially, intrasseously, intrathecally, intraperitoneally, intranasally, intravaginally, rectally, sublingually or subcutaneously, or may be administered by a gastrointestinal, transmucosal or respiratory route. For example, the compound of the present invention or its pharmaceutically acceptable salt may be directly applied to skin. Otherwise, the polypeptide may be prepared into an injectable formulation, and then injected in a predetermined amount into a subcutaneous layer with a 30 gauge thin injection needle, or administered by lightly pricking the skin with the injection needle. Preferably, it may be directly applied to skin. Also, the compound of the present invention or its pharmaceutically acceptable salt may be administered into target cells or tissues (e.g., skin cells or skin tissues) by binding to a molecule causing high affinity-binding or being capsulated within the molecule. The compound of the present invention or its pharmaceutically acceptable salt may be bound to a sterol (e.g., cholesterol), a lipid (e.g., cationic lipid, virosome or liposome) or a target cell specific binding agent (e.g., ligand recognized by a target cell specific receptor) through the technology known in the art. As a coupling agent or a cross-linking agent, for example, protein A, carbodiimide, N-succinimidyl-3-(2-pyridyldithio)propionate (SPDP) or the like, may be appropriately included.

These formulations are disclosed in general reference for pharmaceutical chemistry (*Remington's Pharmaceutical Science*, 15th Edition, 1975, Mack Publishing Company, Easton, Pa.). For reference, nucleotide and protein techniques of the present invention are described in, e.g., Maniatis et al., Molecular Cloning: A Laboratory Manual, Cold Spring Harbor Laboratory, Cold Spring Harbor, N.Y. (1982); Sambrook et al., Molecular Cloning: A Laboratory Manual, 2d Ed., Cold Spring Harbor Laboratory Press (1989); Deutscher, M., Guide to Protein Purification Methods Enzymology, vol. 182. Academic Press. Inc., San Diego, Calif. (1990).

Hereafter, the figures of the present invention will be described.

Figure 2:
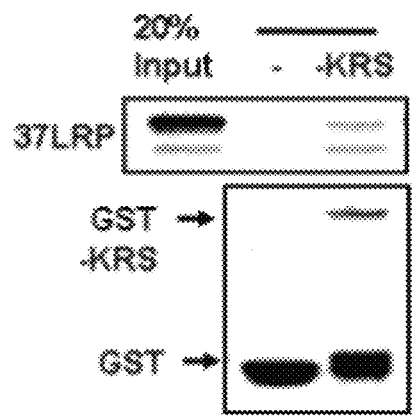
FIG. 2 shows the interaction between human KRS and 37LRP, which was determined by a pull-down assay.
Figure 3:
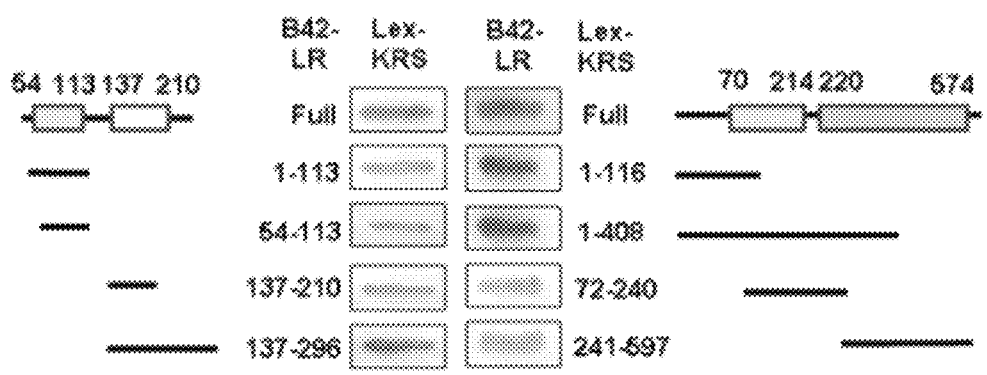
FIG. 3 shows the region of the interaction between human KRS and 37LRP.
Figure 4:
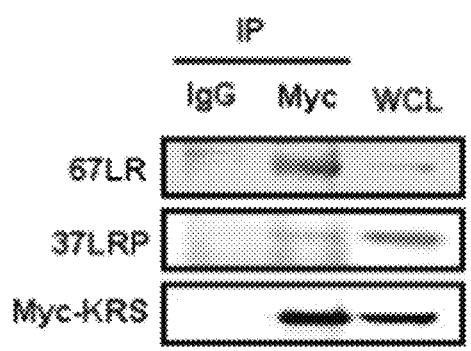
FIG. 4 shows the result when A549 cells transfected with Myc-KRS were subjected to immunoblotting analysis with anti-Myc and anti-laminin receptor antibodies in order to confirm the binding of KRS to 67LR and 37LRP.
Figure 5:
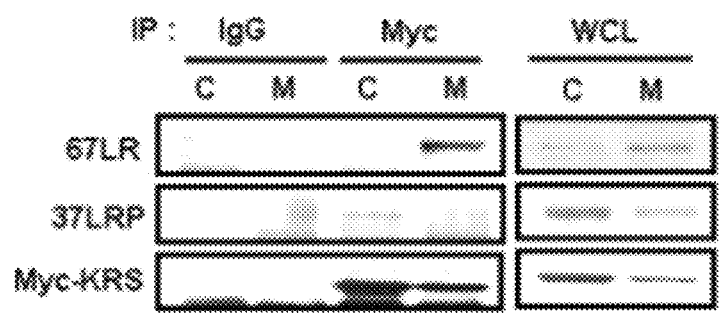
FIG. 5 shows the result when the lysates of A549 cells transfected with Myc-KRS were subjected to western blotting analysis in order to confirm the binding of KRS to 67LR and 37LRP.
Figure 6:
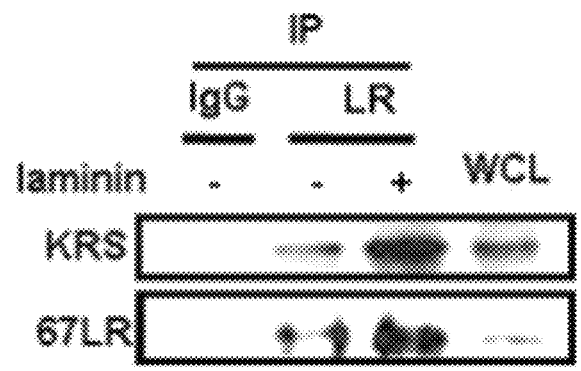
FIG. 6 shows the binding of KRS and 67LR according to laminin treatment, which was identified through immunoprecipitation.

FIGS. 1 to 6 show the specific interaction between human KRS and laminin receptor. In FIG. 1, the interaction between full-length human KRS and 37LRP/p40 was determined by a yeast two-hybrid assay. AIMP1 and AIMP2, the two components of the multi-ARS complex, were used as positive and negative control groups, respectively. The positive interaction is indicated by blue colony formation on a yeast medium containing X-gal. In FIG. 2, 37LRP was synthesized by in vitro translation in the presence of [$^{35}$S]methionine, and subjected to pull-down with GST-KRS or GST. 37LRP co-precipitated with GST-KRS was detected by autoradiography. In FIG. 3, the peptide regions involved in the interaction between KRS and 37LRP were determined by yeast two hybrid assay. 37LRP having 296 amino acids with N-terminal intracellular (amino acids 54 to 113) and C-terminal extracellular (amino acids 137 to 210) domains is divided by a transmembrane domain (amino acids 113 to 137). The N-terminal specific extension (about 70 amino acids) of Human KRS (597 amino acids) is followed by OB-fold anticodon-binding (amino acids about 70 to 214) and catalytic domains (amino acids about 220 to 574). In FIG. 4, A549 cells transfected with Myc-KRS were lysed and subjected to immunoblotting with indicated antibodies (WCL: whole cell lysate). The cells were separated into cytoplasmic and membrane fractions, and immunoprecipitated with anti-Myc antibody. Then, co-precipitation of 67LR and 37LRP was determined by western blotting. IgG was used as a control. In FIG. 5, the lysates of Myc-KRS-transfected A549 cells were subjected to western blotting with the indicated antibodies. The cells were separated into cytoplasmic (C) and membrane (M) fractions, immunoprecipitated with anti-Myc antibody, and co-precipitation of 37LRP and 67LR was determined by western blotting. IgG was used as a control. In FIG. 6, the laminin-dependent interaction between KRS and 67LR was identified by co-precipitation. In other words, it was found that the treatment with laminin (10 μg/ml, 1 h) increased the binding of 67LR and KRS was increased. In order to identify it, immunoprecipitation was performed with 67LR recognizing antibody (abcam, cat # ab2508), and the IgG label at the left side, as total IgG obtained from a rabbit, was used as a negative control. The precipitate was subjected to 10% SDS PAGE, transferred to PVDF membrane, and subjected to immunoblotting with KRS and 67LR recognizing antibodies, respectively.

Figure 7:
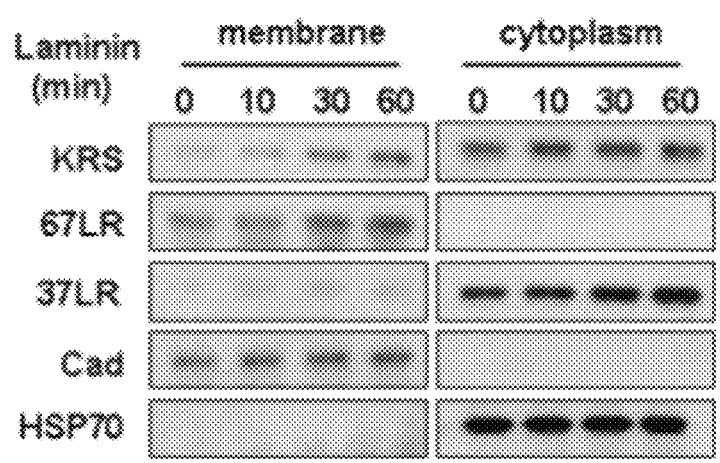
FIG. 7 shows levels of 67LR, 37LRP and KRS in A549 cells treated with laminin, which were determined by western blotting.
Figure 8:
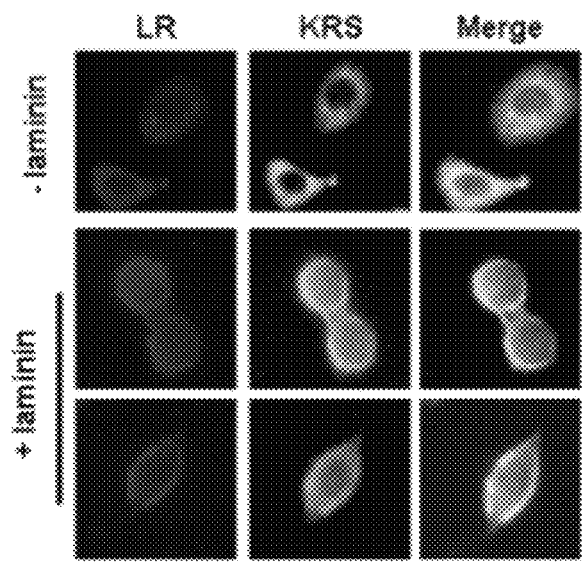
FIG. 8 shows expression of 67LR and KRS in A549 cells treated or untreated with laminin, which was determined by immunofluorescence staining.
Figure 9:
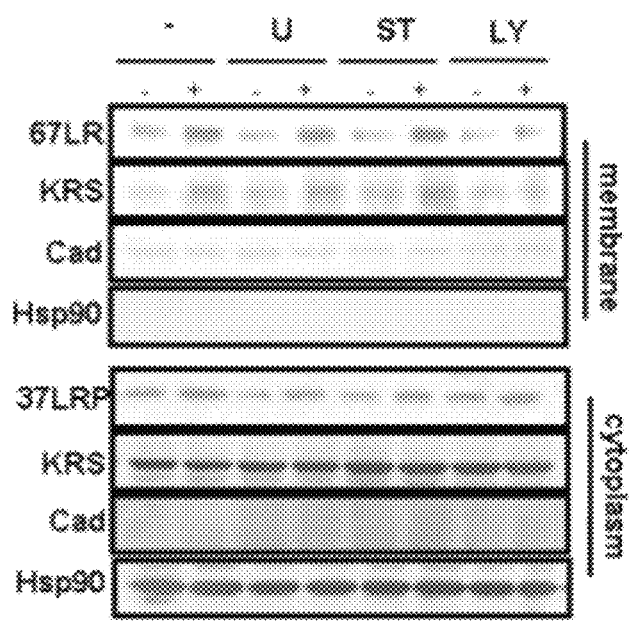
FIG. 9 shows the effect of kinase inhibitors on the cytoplasmic and membrane expression of 67LR and KRS.
Figure 10:
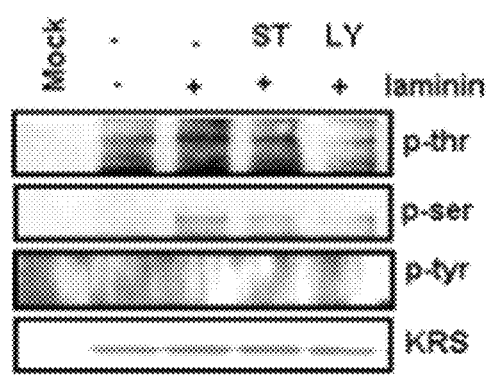
FIG. 10 shows the phosphorylation level in KRS-expressing A549 cells, measured by immunoblotting with p-Thr, -Ser, and -Tyr antibodies, when laminin and kinase inhibitors were treated.
Figure 11:
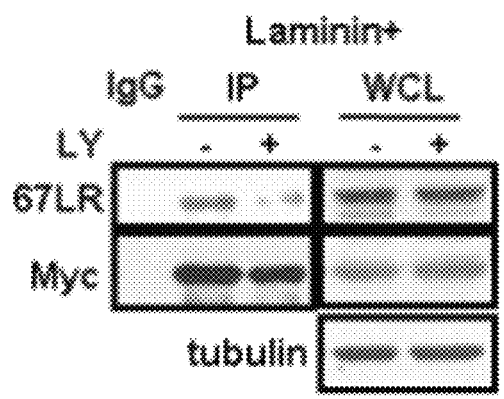
FIG. 11 shows the binding of phosphorylated KRS to 67LR in the KRS expressing A549 cells, which was determined by western blotting.
Figure 12:
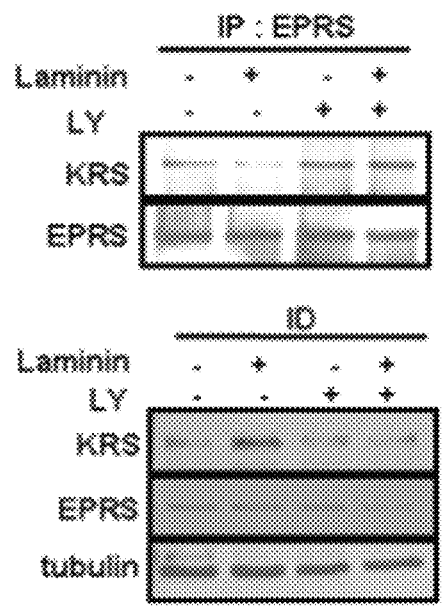
FIG. 12 shows the effect of laminin on the binding of KRS to EPRS, which was determined by western blotting.

FIGS. 7 to 12 show laminin-induced membrane translocation, and phosphorylation of KRS. In FIG. 7, A549 cells were treated with laminin (10 μg/ml), and the levels of 67LR, 37LRP and KRS were determined by western blotting at the indicated times. Hsp90 and cadherin (Cad) were used as markers for cytoplasm and membrane, respectively. In FIG. 8, A549 cells untreated or treated with laminin for 1 hour were subjected to immunofluorescence staining with anti-67LR (MLuC5, Santacruz, sc-59732) (red) and KRS antibodies (green). In FIG. 9, A549 cells were treated with U73122 (U), staurosporin (ST) and LY294002 (LY) that inhibit PLC-gamma, PKC and PI3K, respectively, for 3 hours, and then treated with laminin for 1 hour. Then, it was determined how these kinase inhibitors would affect the cytoplasm and membrane of 67LR and KRS. In FIG. 10, A549 cells were transfected with Myc-KRS, and incubated for 24 hours. Then, the cells were treated with the indicated drugs and then with laminin as above. Myc-KRS was immunoprecipitated, and immunoblotted with anti-p-Thr, -Ser, and -Tyr antibodies. In FIG. 11, A549 cells were transfected with Myc-KRS, and cultured for 24 hours. The transfected cells were pre-treated with LY294002 for 3 hours and then treated with laminin for 1 hour. Myc-KRS was immunoprecipitated, and co-precipitation of 67LR was determined by western blotting. IgG was used as a control for immunoprecipitation. In FIG. 12, A549 cells were cultivated in the presence or absence of laminin and LY294002 as indicated. EPRS (glutamyl-prolyl-tRNA synthetase) was immunoprecipitated with its specific antibody (AbCam), and co-precipitation of KRS was determined by western blotting (upper). The immune-depleted supernatant (ID) was subjected to western blotting with anti-KRS and EPRS antibodies.

Figure 13:
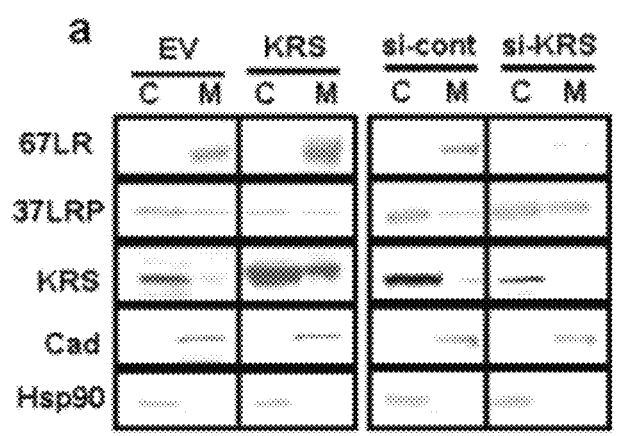
FIG. 13 shows the levels of 67L and KRS in cells transfected with si-control or si-KRS, which were determined by western blotting.
Figure 14:
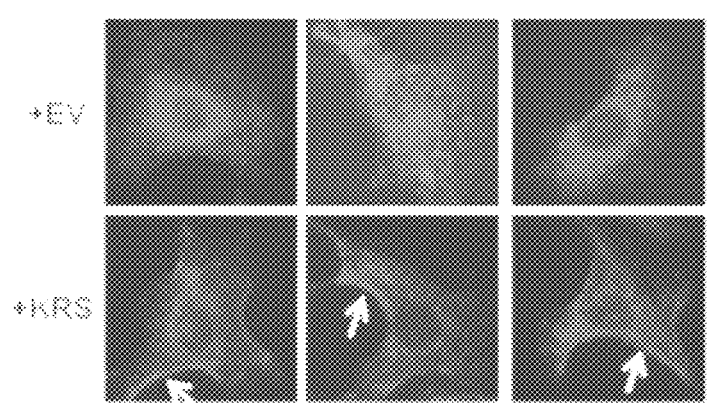
FIG. 14 shows the intracellular distribution of 67LR in A549 cells transfected with EV (empty vector) or KRS, which was determined by immunofluorescence staining.
Figure 15:
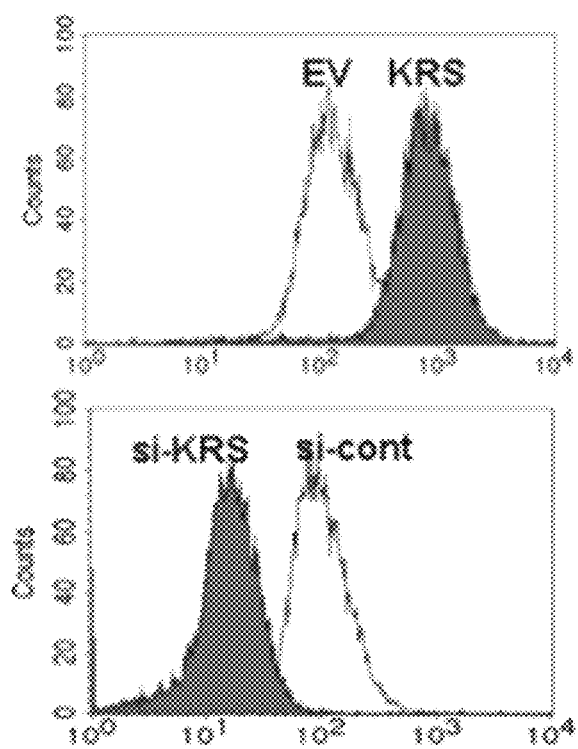
FIG. 15 shows the level of membrane-binding 67LR in A549 cells, which was measured by flow cytometry.
Figure 16:
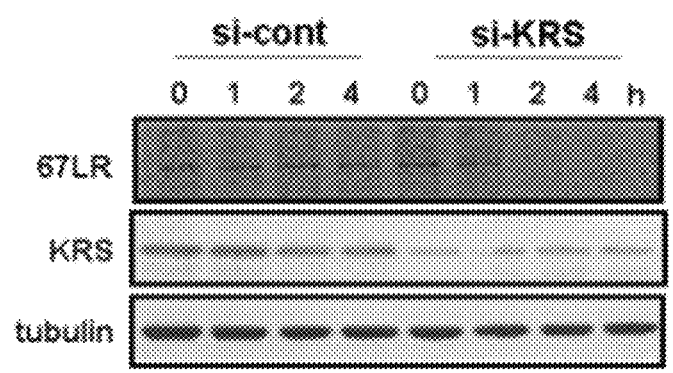
FIG. 16 shows the effect of KRS on cellular stability of 67LR, which was determined by pulse-chase experiment.

FIGS. 13 to 17 show that the level of membrane-bound 67LR depends on KRS. In FIG. 13, A549 cells were transfected with EV, KRS, si-control (si-cont), or si-KRS. The cells were separated into cytoplasm and membrane fractions, and the levels of 67LR and KRS in each fraction were determined by western blotting. Cadherin (red) and hsp90 were used as the markers for cell membrane and cytoplasm, respectively. In FIG. 14, A549 cells transfected with EV (empty vector) or KRS were selected with G418 for 1 week, and intracellular distribution of 67LR was determined by immunofluorescence staining with anti-LR antibody (MluC5). The membrane-located LR was highlighted with arrows. In FIG. 15, in A549 cells, the membrane-bound 67LR level was monitored by flow cytometry using anti-LR antibody (MluC5). The cells were transfected with empty vector or KRS plasmid, and incubated for 24 hours (upper). In order to see the effect of KRS inhibition according to the level of 67LR, the cells were transfected with si-KRS or si-control, and incubated for 48 hours (lower). In FIG. 16, for cellular stability of 67LR, the importance of KRS was determined by a pulse-chase experiment. 293 cells were transfected with si-KRS or si-control, and treated with radioactive methionine for 1 hour. 67LR was immunoprecipitated with an antibody specifically recognizing 67LR (F-18, Santacruz), separated by SDS-PAGE, and, autoradiographed. The inhibition of KRS by its specific siRNA was confirmed by western blotting, and tubulin was used as a loading control.

Figure 17:
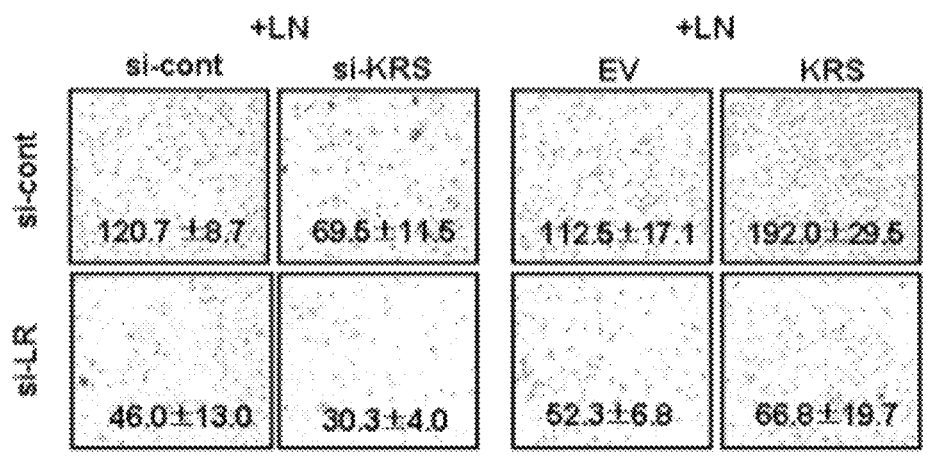
FIG. 17 shows the effect on cell migration when the expressions of KRS and/or 67LR were inhibited.
Figure 18:
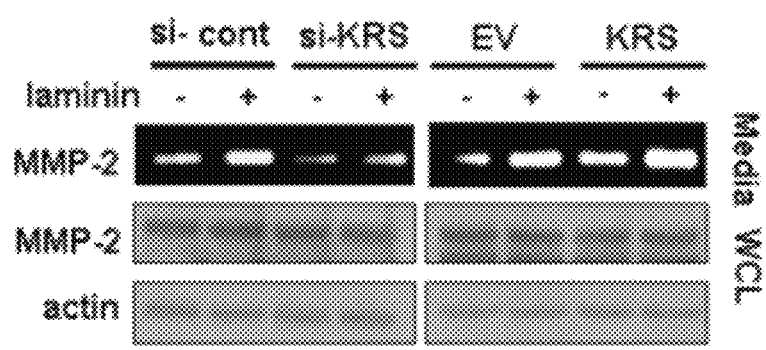
FIG. 18 shows MMP-2 activity and level, measured by zymography and western blotting, when expressions of KRS and/or 67LR were inhibited.
Figure 19:
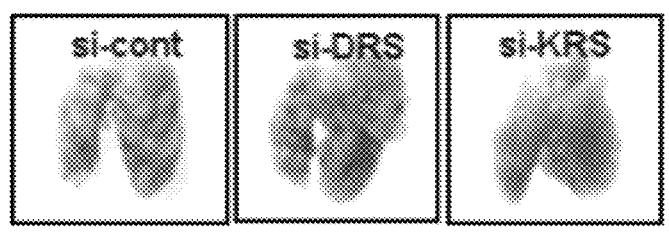
FIG. 19 shows the number of tumor nodules when the expressions of KRS were inhibited in mice transplanted with 4T-1 cell lines.
Figure 19:
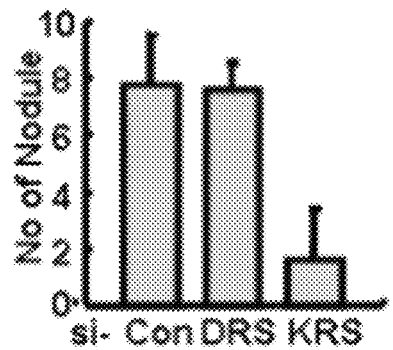
Figure 20:
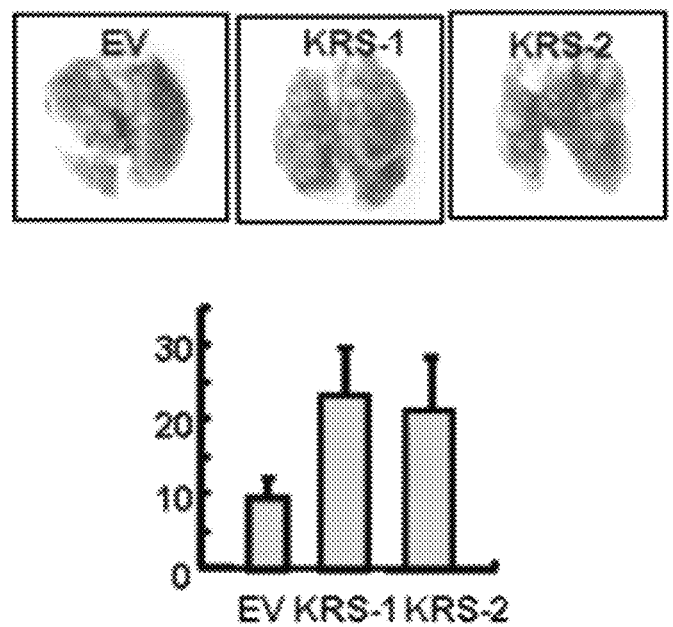
FIG. 20 shows the number of tumor nodules when the expressions of KRS were enhanced in mice transplanted with 4T-1 cell lines.

FIGS. 17 to 20 show that KRS facilitates cell migration and cancer metastasis through 67LR. In FIG. 17, A549 cells were transfected with the indicated plasmids, and incubated in the absence (FIG. 21) or presence (FIG. 17) of laminin, and their effect on cell migration was determined by measuring the migrated cells in a transwell chamber. The number of the cells passed through the membrane was counted and displayed on each panel. The experiment was conducted three times. In FIG. 18, the cells treated as above were used to determine MMP-2 activity and level by zymography (upper) and western blotting (center), respectively. Actin was used as a loading control. In FIG. 19, 4T-1 cells (mammary carcinoma cell line) were transfected with the indicated siRNA, and subcutaneously injected to the back of Balb/C mice. After 27 days, lungs of the mice were extracted, and tumor nodules over 1 mm in diameter were counted. In FIG. 20, two different 4T-1 cells expressing exogenous KRS (KRS-1 and KRS-2) were inoculated as above and after 4 to 5 weeks from the injection, the tumor nodules were counted. The cells transfected with empty vector were used as a control group.

Figure 21:
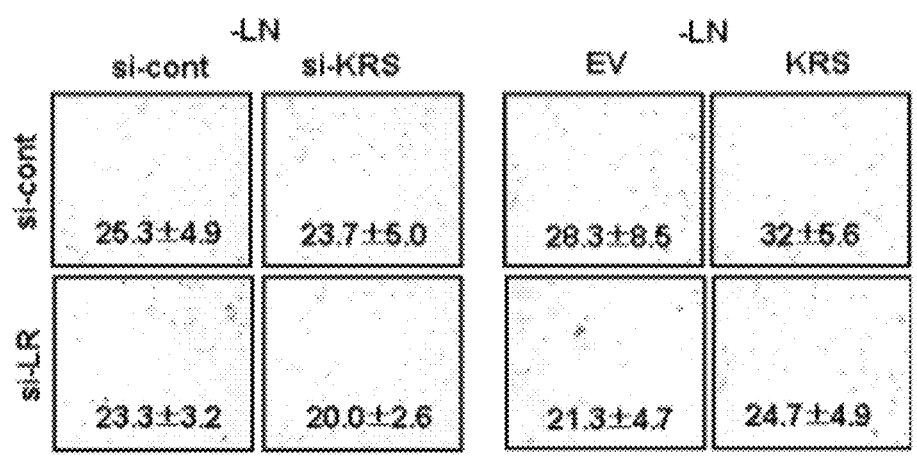
FIG. 21 shows the measurement result of migration of A549 cells incubated in the absence of laminin.
Figure 22:
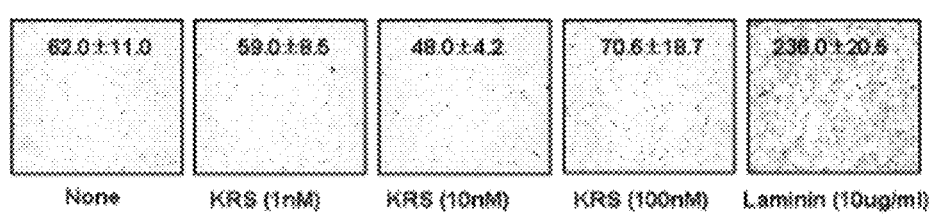
FIG. 22 shows the measurement result of the chemotactic activity of KRS in cell migration.
Figure 23:
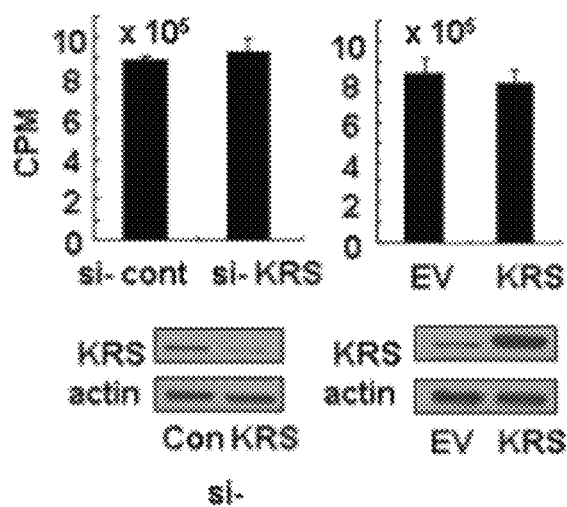
FIG. 23 shows the KRS level and the total intracellular protein synthesis level in A549 cells according to introduction of siRNA and exogenous KRS.
Figure 24:
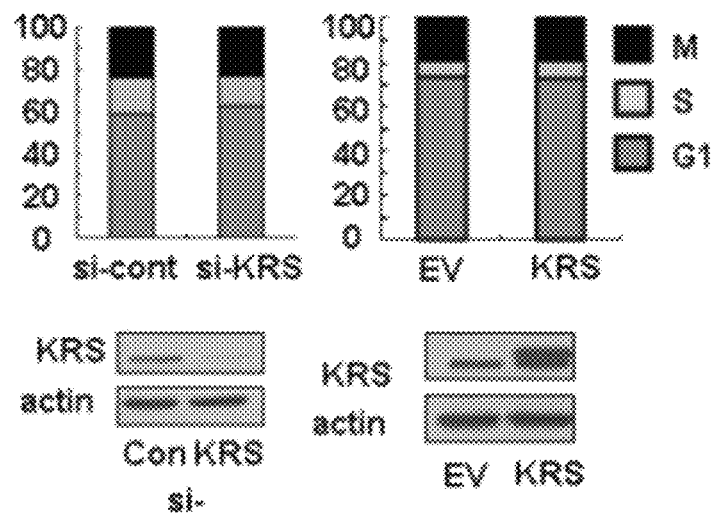
FIG. 24 shows the KRS level and the cell cycle in A549 cells according to introduction of siRNA and exogenous KRS.

FIGS. 21 to 24 show the effect of intracellular and extracellular KRS on cell migration, protein synthesis and cell cycle. In FIG. 21, the migration of A549 cells incubated in the absence of laminin was determined by measuring the migrated cells in a transwell chamber in the same manner as described in FIG. 17. In FIG. 22, in order to see the extracellular chemotactic activity of KRS, the serum-free medium containing KRS at the indicated concentration was placed in the lower chamber of a transwell chamber, and A549 cells were incubated in the upper chamber. Then, the number of migrated calls was counted. In FIG. 23, the level of KRS in A549 cells was down- or up-regulated by introduction of siRNA and exogenous KRS. The transfected cells were incubated for 48 and 24 hours, respectively, and starved in methionine-free medium for 1 hour, and then, were labeled with radioactive-labelled methionine for 2 hours. After being washed, the cells were incubated for 4 hours, and lysed in 0.5% triton X-100 lysis solution, and the radioactivity was measured by a liquid scintillation counter. In FIG. 24, A549 cells were transfected as indicated, fixed, and stained with Propidium iodide, and then analyzed by flow cytometry.

Figure 25:
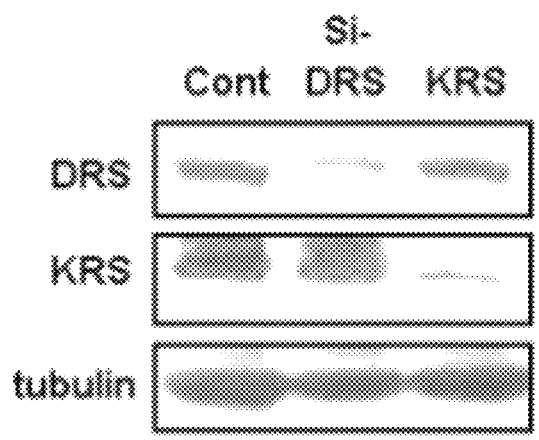
FIG. 25 shows the effect of si-KRS and si-DRS on the expression of their target proteins, which was determined by western blotting.
Figure 26:
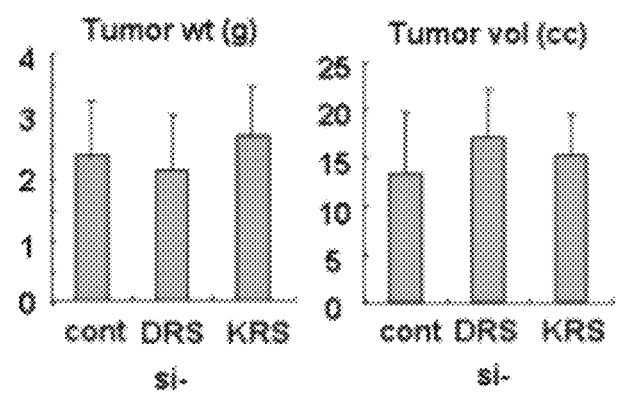
FIG. 26 shows the effect of KRS and DRS inhibition on primary tumor proliferation in tumor cell transplantation.
Figure 27:
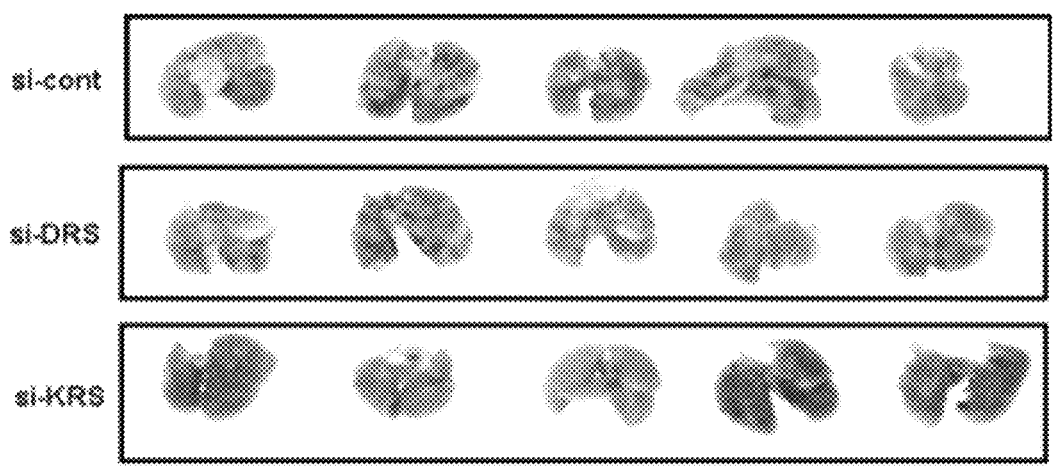
FIG. 27 shows the number of metastatic tumor nodules in tumor cell transplantation.

FIGS. 25 to 27 show the effect of KRS inhibition on cancer metastasis. In FIG. 25, the effect of si-KRS and si-DRS on the expression of their target proteins was determined by western blotting. Tubulin was used as a loading control. In FIG. 26, the siRNA transfected cells ($1 \times 10^6$) were injected as described in the above methods, and after 21 days from the injection, the effect of KRS and DRS inhibition on primary tumor proliferation was determined by measuring the size and volume of a tumor. In each group 6 mice were included (FIG. 19 shows 1 mouse and FIG. 27 shows 5 mice). In FIG. 27, the lungs extracted from the mice were fixed in 10% formalin solution. The number of metastatic tumor nodules is shown in the drawing.

Figure 28:
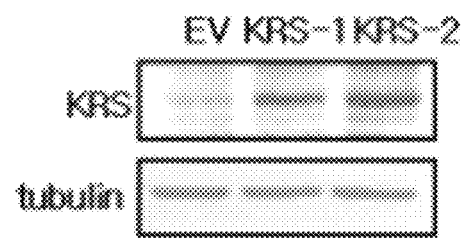
FIG. 28 shows the over-expression of KRS in KRS-1 and KRS-2 cell lines, which was determined by western blotting.
Figure 29:
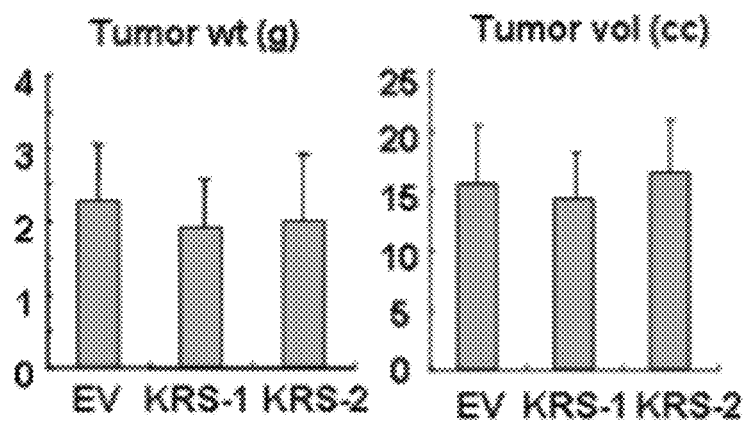
FIG. 29 shows the effect of KRS over-expression on primary tumor proliferation in tumor cell transplantation.
Figure 30:
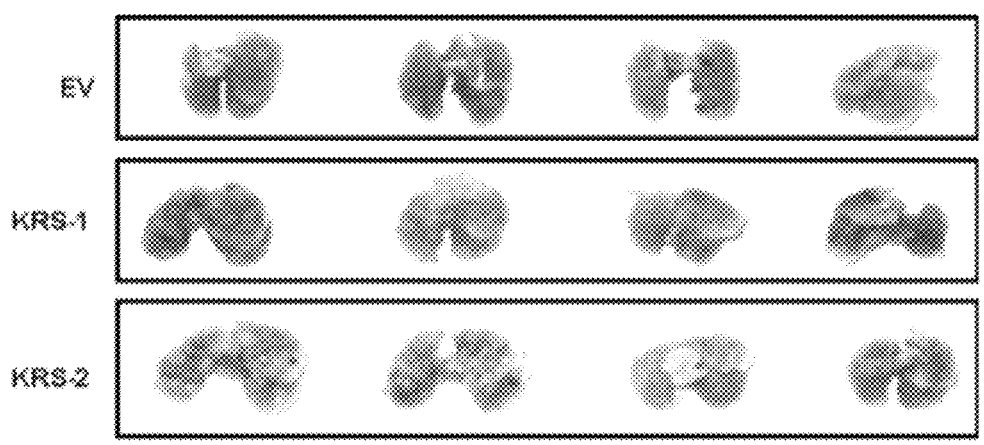
FIG. 30 shows the number of metastatic tumor nodules in tumor cell transplantation.

FIGS. 28 to 30 show the effect of KRS over-expression on cancer metastasis. In FIG. 28, the over-expression of KRS-1 and KRS-2 cell lines was determined by western blotting. In FIG. 29, the effect of KRS over-expression on primary tumor proliferation was compared as above. In FIG. 30, the effect of KRS over-expression on tumor metastasis was determined on day 30 after inoculation. In each group, 4 mice were included (FIG. 20 shows a representative 1 mouse and FIG. 30 shows 4 mice)

Figure 31:
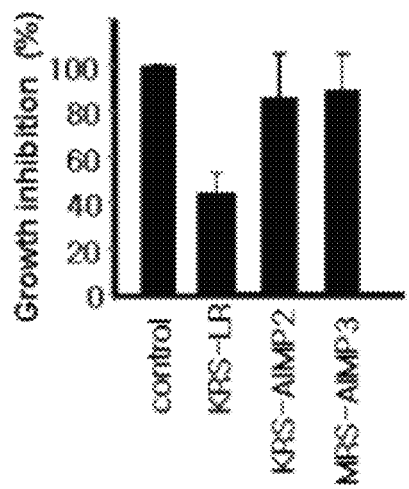
FIG. 31 shows the growth inhibition of yeast cells containing paired proteins (KRS and 67LR (KRS-LR); KRS and AIMP2 (KRS-AIMP2); and MRS and AIMP3 (MRS-AIMP3)) by the compound of the present invention (CAND-KL1, KL1) at 50 μg/ml.
Figure 32:
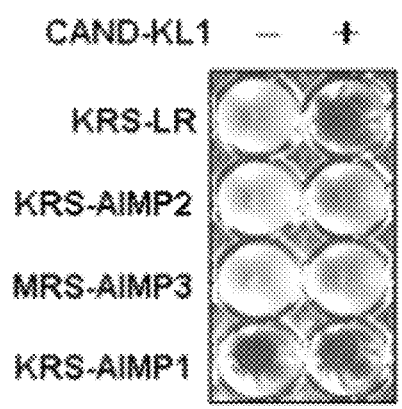
FIG. 32 shows the growth of yeast cells in the presence or absence of the compound of the present invention.
Figure 33:
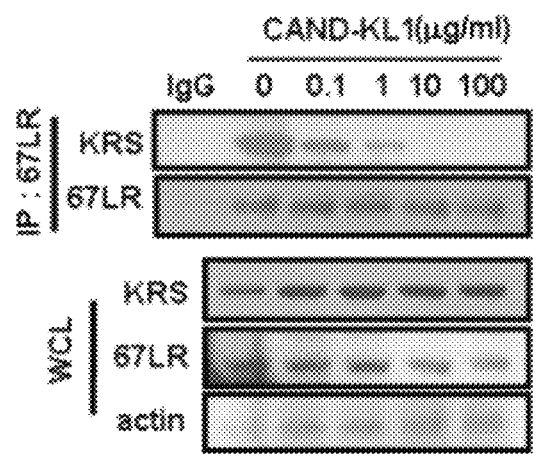
FIG. 33 shows the result when KL1-level-dependent effect on the interaction between KRS and 67LR in 293 cells was tested through co-immunoprecipitation.
Figure 34:
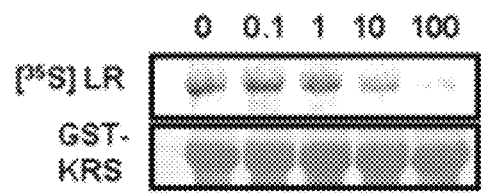
FIG. 34 shows the interaction between KRS and 67LR according to the level of the compound of the present invention, which was determined by co-precipitation of 67LR and KRS.
Figure 35:
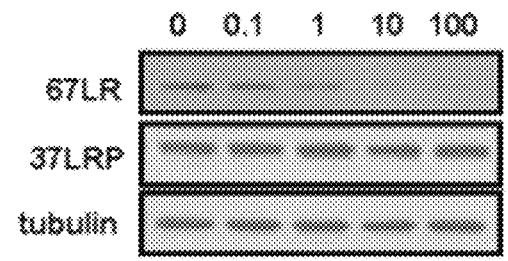
FIG. 35 shows the effect of the compound of the present invention on the intracellular level of 67LR and 37LRP in A549 cells, which was determined by western blotting.
Figure 36:
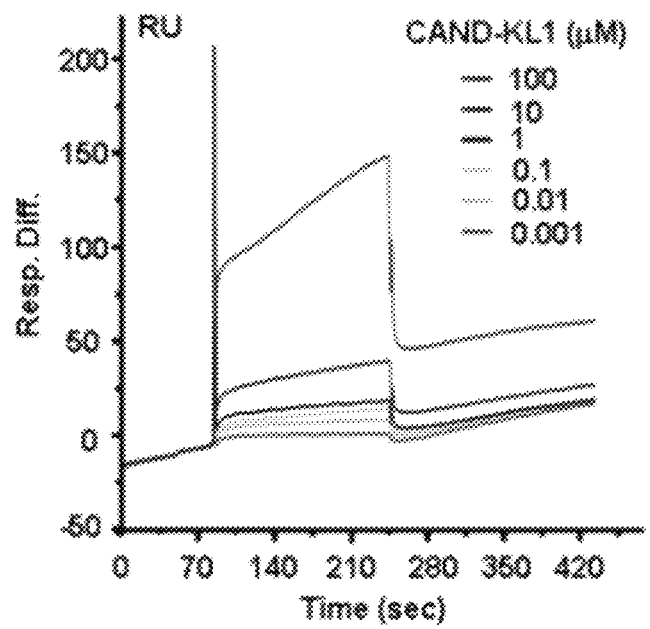
FIG. 36 shows the interaction between KRS and the compound of the present invention, which was determined by a surface plasma on resonance method.

FIGS. 31 to 36 show the effect of a compound on the inhibition of the interaction between KRS and 67LR, and the intracellular stability of 67LR. FIG. 31 shows the growth inhibition of yeast cells containing indicated paired proteins by the compound represented by Formula 15 (CAND-KL1, KL1) at 50 µg/ml. As a control, an OD level of cells treated with DMSO was measured. FIG. 32 is a photograph showing cell growth in wells containing yeast cells having indicated interaction pairs in the presence or absence of CAND-KL1. In FIG. 33, in 293 cells, through co-immunoprecipitation, the KL1-dose-dependent effect on the interaction between KRS and 67LR was tested. The cells were treated with KL1 for 3 hours, 67LR was immunoprecipitated, and co-precipitation of KRS was determined by western blotting. In FIG. 34, in the presence of KL1 in indicated levels, a laminin receptor labeled with radioisotope was mixed with GST-KRS (1 µg). GST-KRS was precipitated with glutathione-Sepharose beads, and co-precipitated laminin receptor was detected with autoradiography. In FIG. 35, in A549 cells, the effect of KL1 on the intracellular level of 67LR and 37LRP was tested with western blotting. In FIG. 36, the interaction between KRS and CAND-KL1 was tested by a surface plasmon resonance method as described in an experimental method. GST-KRS was immobilized on a CM5 Sensor Chip, and the binding was measured by a resonance unit (RU) at indicated concentrations (indicated by different colors). GST protein was used as a control so as to measure KRS-specific binding affinity. The apparent binding constant was obtained by using a BIA evaluation program.

Figure 38:
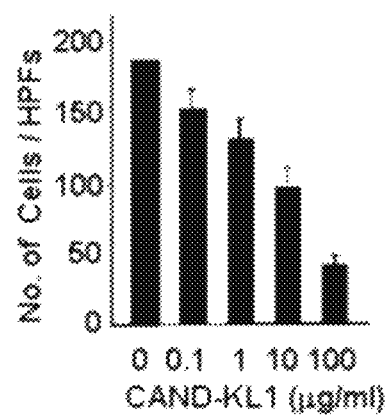
FIG. 38 shows the effect of the compound of the present invention on cell migration.
Figure 39:
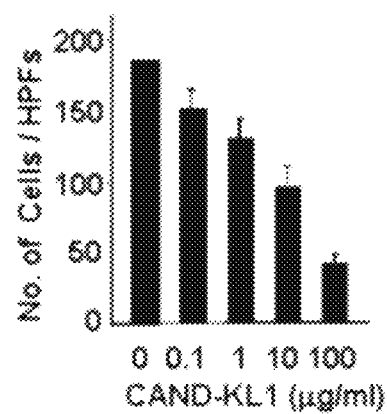
FIG. 39 shows the effect of the compound of the present invention on cell migration, which was quantitatively determined.
Figure 40:
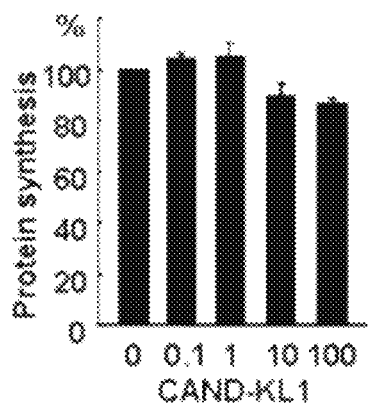
FIG. 40 shows the effect of the compound of the present invention on protein synthesis of cells.
Figure 41:
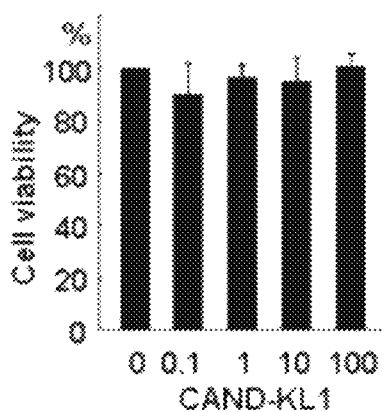
FIG. 41 shows cytotoxicity of the compound of the present invention, which was determined by using A549 cells.
Figure 42:
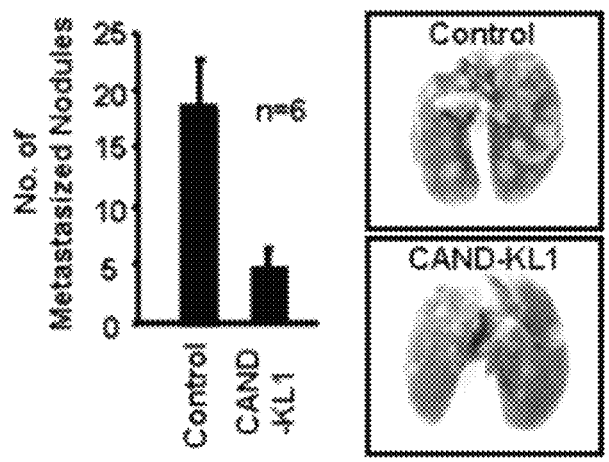
FIG. 42 shows the effect of the compound of the present invention on cancer metastasis.
Figure 43:
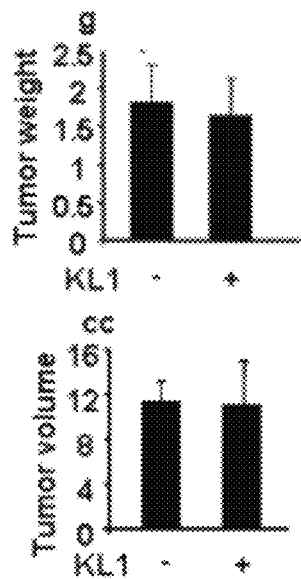
FIG. 43 shows the effect of the compound of the present invention on the weight and volume of primary tumor.

FIGS. 37 to 43 show that inhibition of KRS-laminin receptor can inhibit cell migration and cancer metastasis. On MMP2 activity (FIG. 37) and cell migration (FIGS. 38 and 39), KL1-dose-dependent effect was measured. For the test on the cell migration, the cells were treated with KL1 for 8 hours. In FIG. 40, in order to see the effect of KL1 on protein synthesis of cells, A549 cells were treated with KL1 at indicated concentrations, and starved in methionine-free medium. Then, [$^{35}$S] methionine was added thereto for 2 hours. Then, the cells were incubated in complete medium for 4 hours, and the level of added methionine was measured by a scintillation counter. In FIG. 41, KL1-dose-dependent cytotoxicity was measured by using A549 cells. In FIG. 42, the effect of KL1 on cancer metastasis was measured according to the method as described above. In each group, 6 mice were included, and KL1 was abdominally injected for 3 weeks, in a dose of 30 mg/kg once a day. Then, the mice were sacrificed. The metastasized tumor nodules over 1 mm in diameter were counted, and their average was calculated (left). The photograph of a representative lung is shown at the right side. In FIG. 43, on a KL1 treated group and a KL1 non-treated, primary tumors were observed. As a result, it was determined that between two groups, there is no significant difference in weight and size.

Advantageous Effects

The present inventors confirmed that KRS has an effect on cancer metastasis by facilitating cancer (or tumor) cell migration through interaction with 67LR, and also found that a substance inhibiting the interaction between KRS and 67LR can prevent and treat cancer by inhibiting cancer cell metastasis. Accordingly, the composition of the present invention can inhibit cancer metastasis, and thus provide a novel means for prevention and treatment of cancer.

Examples

Hereinafter, the present invention will be described in detail with reference to Examples. However, Examples below are for illustrative purpose only and are not constructed to limit the scope of the present invention.

<Experimental Method>

1. Cell Culture and Materials

A549 and HEK293 cells were purchased from ATCC. Mouse mammary carcinoma 4T-1 cell line was provided by Dr. Kim Sung-jin (Gachon medical school). RPMI (for A549 and 4T-1 cells) and DMEM (Dulbecco's Modified Eagle Medium, for the other cells), containing 10% fetal bovine serum (FBS) and 1% antibodies were used for cell cultivation. PcDNA3.1 vector encoding 37LRP was provided from Dr. Tachibana Hirofumi (Kyushu University). Myc-tagged human KRS and DRS were cloned at the EcoRI/XhoI restriction enzyme site of the pcDNA3 vector. Murine KRS cDNA was obtained by RT-PCR, and cloned at HindIII/XhoI restriction enzyme site of the pcDNA3.1 vector. siRNA targeting murine and human KRS and DRS were purchased from Invitrogen. Sequences for siRNAs would be provided upon request. Gene porter (GTS) and lipopectamine 2000 (invitrogen) were used as transfect reagents. LY294002, U73122 and staurosporin were purchased from Calbiochem, and cycloheximide and laminin (Engelbreth-Holm-Swarm murine sarcoma) were purchased from Sigma.

2. Immunoprecipitation and Western Blotting

The cells were lysed with 20 mM Tris-HCl buffer (pH 7.4, lysis buffer) containing 150 mM NaCl, 0.5% triton X-100, 0.1% SDS and protease inhibitor. The protein extracts were incubated with normal IgG and protein G agarose for 2 hours, and then centrifuged to remove proteins non-specifically bound to IgG. The present inventors mixed the supernatants with purified 67LR antibody (F-18, Santacruz), incubated for 2 hours at 4° C. with agitation, and added protein A agarose thereto. After washing three times with ice-cold lysis buffer, the precipitates were dissolved in the SDS-sample buffer, and separated by SDS-PAGE. In order to determine the binding of KRS and LR in different cell fractions, they transfected pcDNA3.1-Myc-KRS, and separated the plasma membrane and cytoplasmic fractions by using the proteoextract kit (Calbiochem) in accordance with the manufacturer's instruction. Then, co-immunoprecipitation was performed as described above. In order to analyze protein levels, the proteins were extracted from the cells, and were separated by 10% SDS-PAGE. Unless specified, anti-LR antibody (Abcam, ab2508) was used for simultaneous immunoblotting of 37LRP and 67LR. Antibodies for hsp90 and Pan-cadherin were purchased from Santacruz.

3. Flow Cytometry

In order to address a cell cycle, the cultivated cells were transfected or treated with the indicated vector or compounds, fixed with 70% ethanol at 4° C. for 1 hour, and washed with ice-cold PBS twice. Then, the cells were stained with propidium iodide (50 µg/ml), 0.1% sodium citrate, 0.3% NP40, and RNaseA (50 µg/ml) for 40 minutes, and subjected to flow cytometry (FACS Calibur, Beckton-Dickinson). For each sample, 20000 cells were analyzed by using Cell Quest Pro software. For the analysis of the amount of 67 kD LR on a Cell surface, $1\times10^6$ cells were incubated with IgG or anti-LR antibody (MLuC5, 1 µg) recognizing extracellular domain of 67LR, and then with FITC secondary antibody. After being washed with PBS, the samples were scanned by FACS.

4. Immunofluorescence Staining

A549 cells on a 9 mm cover slip were fixed with 70% methylalchol, and shortly washed with cold PBS. After incubation with blocking buffer containing 1% CAS, 3% BSA and 0.5% triton X-100 for 30 minutes, the cells were incubated with antibody (Abcam) against KRS, and antibody (Santacruz) against MLuC-5 for 1 hour. Alexa 488 and 568 (invitrogen) were added thereto, and treated at room temperature for 30 minutes. After being washed with cold PBS for 30 minutes, specimens were monitored by laser scanning microscopy.

5. Pulse-Chase Experiment 293 cells were transfected with si-KRS or si-control (invitrogen) by using lipopectamine 2000. The cells were incubated with methionine-free medium for 1 hour, added with [$^{35}$S] methionine (50 µCi/ml), and incubated for 1 hour. After radioactive methionine was washed off with fresh medium, 67LR was immunoprecipitated with its specific antibody (Santacruz), separated by 12% SDS-PAGE, and subjected to autoradiography using BAS (FLA-3000, Fujifilm). The amount of 67LR was measured by Multi-gauge program (V3.0, Fujifilm).

6. Yeast Two Hybrid Assay cDNAs encoding different fragments of human KRS were obtained by PCR with the corresponding primers. The PCR product for KRS was digested with EcoRI and XhoI, and ligated with the corresponding sites of pEG202 vector (for the construction of LexA-fusion proteins) and pJG4-5 vector (for the construction of B42-fusion proteins). The cDNAs encoding 37LRP fragments were provided from Dr. Barbara J. Ballermann (Alberta University), and were subcloned at EcoRI and XhoI sites of pJG4-5 vector. The interactions between the two fusion proteins were analyzed by the formation of blue colonies on the X-gal-containing yeast medium.

7. In Vitro Binding Assay

The present inventors expressed GST-KRS or GST in *E. coli* Rosetta (DE3) strain, and mixed the protein extracts with glutathione-Sepharose in PBS buffer containing 1% Triton X-100 and 0.5% N-laurylsarcosine at 4° C. for 2 hours. They synthesized human 37LRP by in vitro translation in the presence of [$^{35}$S]methionine by using TNT Quick coupled Transcription/Translation system (Promega) and using pcDNA3-37LRP as the template. The synthesized 37LRP was added to the GST protein mixtures above, incubated at 4° C. for 4 hours with agitation in the PBS buffer containing 1% Triton X-100, 0.5% N-laurylsarcosine, 1 mM DTT, 2 mM EDTA and 300 µM phenylmethylsulfonyl fluoride, and washed with the same buffer containing 0.5% Triton X-100 6 times. Then, they eluted the proteins bound to sepharose beads with the SDS sample buffer, separated by SDS-PAGE, and carried out radiation measurement (autoradiograph).

8. Cell Migration Assay

Cell migration was measured by using 24-well transwell chambers with polycarbonate membranes (8.0 µm pore size, Costar) as previously described (Park, S. G. et al. Human lysyl-tRNA synthetase is secreted to trigger pro-inflammatory response, *Proc. Natl. Acad. Sci. USA* 102, 6356-6361 (2005)). A549 cells were suspended in serum-free RPMI medium and added to the upper chamber at a concentration of $1\times10^5$ cells per well. Each of the purified human KRS at the indicated concentrations, laminin (10 µg/ml) or gelatin (10 µg/ml) was placed in the lower well, and the cells were allowed to migrate for 6 hours at 37° C. in a $CO_2$ incubator.

The cells were fixed with PBS containing 70% methyl alcohol for 30 minutes and washed with PBS three times. The cells were stained with hematoxylin (Sigma) for 10 minutes and washed with distilled water. The non-migrated cells were removed from the upper portion of the membrane with a cotton swab. The membranes were separated from the chamber, and mounted to Gel Mount (Biomeda, USA). The migrated cells (attached to the lower face of the membrane) were counted at four randomly selected sites by a microscope (×20).

9. Zymography

A549 cells were transfected with the plasmids encoding the indicated siRNAs and recombinant KRS (or DRS) were incubated for 48 and 24 hours, respectively, and were inoculated to RPMI medium containing 10% FBS ($1 \times 10^5$ cells/well). The cells were starved in serum-free RPMI medium for 2 hours, added with laminin, and incubated for 24 hours at 10 µg/ml. 20 µl of the culture medium was mixed with 5×FOD buffer (0.125M Tris-HCl, pH 6.8, containing 4% SDS, 20% glycerol, and 0.01% bromophenol blue), and subjected to 10% SDS-PAGE containing 1 mg/ml of gelatin. The gel was washed with 2.5% triton X-100 twice, each time for 20 minutes, then with distilled water twice, each time for 20 minutes, and incubated with reaction buffer (50 mM Tris-HCl, pH 7.5, containing 10 mM $CaCl_2$, 150 mM NaCl, 1 µM $ZnCl_2$, 1% Triton X-100, and 0.002% sodium azide) for 24 hours at 37° C. The gel was washed with distilled water, and stained with coomassie blue R250, and destained with 35% methanol.

10. In Vivo Cancer Metastasis Experiment

Mouse mammary carcinoma 4T-1 cells were transfected with si-KRS, si-DRS or si-control, and incubated for 24 hours. The cells ($1 \times 10^6$) were subcutaneously injected into the back of 6-week old female Balb/c mice. The effect of si-RNAs on their target gene expression was tested in the remaining cells after 48 hours from the transfection, and also in the primary tumors from 3 to 10 days at 2 day intervals after the injection by western blotting with their corresponding antibodies. The growth of a tumor was monitored by measuring a tumor size three times per week. The whole body weights were also simultaneously measured. The mice were sacrificed on day 21 after the injection, and the primary tumors and lungs were extracted from the mice. The lungs were fixed in 10% formalin for 24 hours. The number and size of metastatic tumor nodules in lungs were measured, and tumor nodules of larger than 1 mm in diameter were separately recorded. The primary tumors were also weighed. In order to examine the effect of KRS over-expression on cancer metastasis, murine KRS vector or empty vector were transfected into 4T-1 cells, and stable transfectants were selected by the incubation in the presence of G418 for 3 weeks. Then, the inventors picked up several single colonies, and compared the KRS expression level by western blotting. Two different colonies (KRS-1 KRS-2) expressing KRS at a higher level than the control group cells were selected, and used for injection. All processes were performed as described above except that the mice were sacrificed after 30 days from the injection.

11. Cancer Metastasis Inhibitory Activity Test

On the compound of the present invention obtained by screening a library of compounds, the extent of inhibition on the interaction between KRS and laminin receptor (67LR) was determined by a yeast two hybrid assay, as described below. KRS, LR, AIMP2, AIMP3 and MRS were cloned at LexA vector (clontech) and B42 vector (clontech) each so as to produce required vectors. From among the vectors, LexA-KRS vector and B42-LR vector were co-transformed into yeast EGY/SH cells, and then the yeast cells were diluted to an absorbance (540 nm wavelength) of 0.2 in galactose medium not containing uracil (Ura), histidine (His), tryptophane (Trp) and leucine (Leu), and placed in an amount of 200 u in a 96 well plate. 1 µl of each compound at a concentration of 10 mg/ml was placed in each well, incubated for 6 days, and the absorbance was measured at 540 nm. The present inventors selected a compound which showed a reduction in growth by 50% or more as compared to a control group. The inhibitory specificity of the selected compound was tested by using two different interaction pairs such as LexA-KRS/B42-AIMP2 and LexA-MRS/B42-AIMP3.

12. Cell Protein Synthesis

A549 cells were treated with the compound (2-[2-(4-methyl-benzoylimino)-benzothiazole-3-yl]-butyric acid, CAND-KL1 or KL1) represented by Formula 15, at indicated concentrations. Then, the cells were cultivated in methionine-free medium for 30 minutes, added with [$^{35}S$] methionine (10 mCi/ml), and cultivated for 2 hours. The cells were again cultivated in completed medium for 4 hours, and collected. They were lysed, and the radiation dose of lysed cells was measured by a scintillation counter.

13. Cytotoxicity Analysis $10^4$ A549 cells were placed in a 96-well plate, and treated with the compound represented by Formula 15, at indicated concentrations for 24 hours. Then, EZ-cytox (Daeil Lab, Korea) compound was added in an amount of 10 µl to each well in accordance with the manufacturer's instruction, followed by cultivation for 2 hours. A microplate reader was used to measure the absorbance at 420 nm.

14. Surface Plasmon Resonance Assay

The interaction between KRS and the compound (Formula 15) was tested by BIAcore3000 (GE healthcare). GST and GST-KRS were diluted to 20 µg/ml in 10 mM sodium acetate (pH 5.0). Then, each protein was immobilized on the surface of a CM5 sensor chip (GE healthcare). CAND-KL1 was diluted to indicated concentrations with PBS containing 1% DMSO, and injected at 25° C. at a rate of 20 µl/min. Then, the binding was measured by a change in a resonance unit (RU). The specific binding activity of CAND-KL1 to GST-KRS was measured by subtracting binding to GST in sensorgram. The apparent binding constant was obtained through 1:1 binding by moving a baseline in a BIA evaluation program.

<Test Result>

1. Specific Interaction between KRS and 67LR

The specific interaction between full length KRS and 37LRP was confirmed by a yeast two hybrid assay. LexA-KRS generated blue colonies when paired with B42-37LRP as well as AIMP2, the known partner of KRS (Kim, J. Y. et al. p38 is essential for the assembly and stability of macromolecular tRNA synthetase complex: Implications for its physiological significance, Proc. Natl. Acad. Sci. USA 99, 7912-7916 (2002)), but not with AIMP1 (FIG. 1). In vitro binding assay, [$^{35}S$]methionine-labelled 37LRP was mixed with either GST-KRS or GST, precipitated with glutathione-Sepharose, and subjected to autoradiography. 37LRP was co-precipitated with GST-KRS, but not with GST (FIG. 2). Deletion mapping by the yeast two hybrid assay determined that the N-terminal extension of human KRS and the C-terminal extracellular domain of LR are involved in their association (FIG. 3).

Since cytoplasmic 37LRP is converted into membrane-embedded 67LR, the present inventors determined whether KRS would differently bind between 37LRP and 67LR. Myc-KRS was introduced into lung carcinoma A549 cells and immunoprecipitated with anti-Myc antibody. When the cell lysate was subjected to western blotting, 67LR existed at a lower level than 37LRP (see the right column in FIG. 4). However, Myc-KRS was more predominantly bound to 67LR than 37LRP (see the center column in FIG. 4). The present inventors then separated A549 cells into cytoplasmic and plasma membrane fractions, and determined the interaction of Myc-KRS with 37LRP and 67LR. 37LRP and 67LR were mainly detected at cytoplasm and plasma membrane, respectively (see the right side in FIG. 5), while KRS existed at both fractions although a major portion was observed at cytoplasm. When both fractions were subjected to immunoprecipitation with anti-Myc antibody, the membrane-bound 67LR was mainly co-precipitated with KRS although a low amount of 37LRP in cytoplasm was also precipitated, (see the left side in FIG. 5). This result indicates that KRS can potentially bind to both types of laminin receptor, but prefers intracellular binding to 67LR. Then, the present inventors investigated whether laminin treatment has an effect on the interaction between KRS and 67LR. The interaction between two proteins was increased by laminin treatment (see FIG. 6)

2. KRS Phosphorylation and Dissociation from Multi-tRNA Synthetase Complex are Involved in Laminin-Dependent Membrane Translocation of KRS.

The present inventors then investigated whether intracellular distribution of KRS is changed by laminin treatment in A549 cells through cell fractionation and immunofluorescence staining. After laminin treatment, the membrane level of KRS and 67LR was gradually increased with little changes in the cytoplasmic KRS and 37LRP level or their expression (FIG. 7, data not shown). Immunofluorescence staining also demonstrated the shift of 67LR and KRS toward membrane side by laminin treatment (see FIG. 8, red and green, respectively). The present inventors then investigated whether membrane translocation of KRS is physiologically adjusted by signal transduction triggered by laminin. A few different kinases such as phosphoinositide 3-OH kinase (PI3K) (Shaw, L. M., Rabinovitz, I., Wang, H. H., Toker, A. & Mericurio. A. M. Activation of phosphoinositide 3-OH kinase by the alpha6beta4 integrin promotes carcinoma invasion. *Cell* 91, 949-960 (1997)), protein kinase C (PKC) (Li, Y. Q. et al. Protein kinase C mediates the signal for interferon-gamma mRNA expression in cytotoxic T cells after their adhesion to laminin. *Immunology* 93, 455-461 (1998)), and phospholipase C-gamma (PLC-gamma) (Vossmeyer, D., Hofmann, W., Loster, K., Reutter, W. & Danker, K. Phospholipase C-gamma binds alpha1beta1 integrin and modulates alpha1beta1 integrin-specific adhesion. *J. Biol. Chem.* 277, 4636-4643 (2002); Kanner, S. B., Grosmaire, L. S., Ledbetter, J. A. & Damle, N. K. Beta 2-integrin LFA-1 signaling through phospholipase C-gamma 1 activation. *Proc. Natl. Acad. Sci. USA* 90, 7099-7103 (1993)) are known to be activated by laminin. In order to see whether any of these kinases are involved in laminin-dependent membrane translocation of KRS, the present inventors blocked each of these kinases with their specific inhibitors, and checked how these treatments would affect the laminin-dependent membrane translocation of KRS. Laminin-dependent increase of KRS and 67LR in the membrane fraction was inhibited in the presence of LY294002 (PI3K inhibitor) while the cells treated with U73122 or staurosporin showed a larger laminin-dependent increase of 67LR than those in the control group (the upper side in FIG. 9, data not shown). None of these kinases affected the intracellular level of KRS (the lower side in FIG. 9). These results imply that PI3K should be involved in laminin-induced phosphorylation of KPS. In fact, phosphorylated KRS at threonine and serine, but not at tyrosine, was increased by laminin treatment, but blocked in the presence of LY294002, while staurosporin did not have any effect (FIG. 10). The present inventors also checked whether the laminin-induced phosphorylation of KRS would be necessary for its interaction with 67LR. The treatment of LY294002 inhibited the laminin-induced association of KRS with 67LR (FIG. 11). Since cytoplasmic KRS is anchored to the multi-ARS complex, the present inventors also checked whether laminin-dependent phosphorylation of KRS would affect its association with the multi-ARS complex by co-immunoprecipitation of KRS with glutamyl-prolyl-tRNA synthetase (EPRS), another enzyme component of the complex. In the absence of LY compound (LY294002), laminin treatment decreased the association of KRS with EPRS, and at the same time increased KRS in immuno-depleted soluble fraction (left lanes in upper and lower panels in FIG. 12). On the other hand, the KRS bound to EPRS was not affected by laminin treatment when the cells were pre-treated with LY294002 (right lanes in upper and lower panels in FIG. 12). This indicates that the phosphorylation of KRS is necessary for the laminin-dependent dissociation of KRS from the complex.

3. KRS is Required for Intracellular Stability of 67LR.

The present inventors then checked whether KRS would affect the membrane level of 67LR in A549 cells. The 67LR level in plasma membrane was increased by KRS (see the left side in FIG. 13), but the laminin effect was abolished when KRS was suppressed with its specific siRNA (see the right side in FIG. 13). This indicates the importance of KRS in laminin-dependent enhancement of 67LR. The intracellular distribution of laminin receptor was compared between A549 cells transfected with empty vector (EV) or KRS by immunofluorescence staining. Laminin receptor was strongly stained in cell membrane regions in KRS overexpressing cells compared to those in the control group (FIG. 14). The present inventors also investigated 67LR existing in the membrane by flow cytometry. The membrane level of 67LR was increased when KRS was supplied from the outside, and on the other hand, the level was decreased when KRS was inhibited by si-KRS (FIG. 15).

The present inventors investigated how KRS enhances membrane level of 67LR. Theoretically, KRS can facilitate the 67LR through transcription or conversion from 37LRP. However, transfection of KRS did not increase LR transcription, excluding its temporary role in the LR transcriptional control (data not shown). The present inventors also checked whether KRS would mediate fatty acylation of 37LRP since 37LRP modification is known to be prerequisite for the conversion of 37LRP to 67LR (Landowski, T. H., Dratz, E. A. & Starkey, J. R. Studies of the structure of the metastasis-associated 67 kDa laminin binding protein: fatty acid acylation and evidence supporting dimerization of the 32 kDa gene product to form the mature protein. *Biochemistry* 34, 11276-11287 (1995); Buto, S. et al. Formation of the 67-kDa laminin receptor by acylation of the precursor. *J. Cell. Biochem.* 69, 244-251 (1998)). As a result, KRS did not affect the fatty acylation of 37LRP at all (data not shown). The present inventors also investigated the effect of KRS on metabolic turnover of 67LR by a pulse-chase experiment. Initial protein synthesis was labeled with radioactive methionine, and then blocked with cycloheximide. Then, disappearance of 67LR was monitored by autoradiography at a time interval. 67LR was rapidly decreased when KRS was suppressed with its siRNA, whereas its level was well sustained in si-control cells during this time frame (FIG. 16).

Thus, KRS seems to extend the half life of 67LR through its association with 67LR in plasma membrane.

4. KRS Increases Cell Migration and Cancer Metastasis through 67LR.

The inventors then investigated whether KRS expression level would affect laminin-dependent A549 cell migration by using transwell membrane assay. Migration of the control group cells was enhanced about 6 times on average by laminin treatment (FIGS. 21 and 17). However, the laminin-dependent cell migration was reduced when KRS was suppressed with its si-RNA (FIG. 17, si-control and si-KRS). On the other hand, KRS over-expression increased cell migration facilitated by laminin treatment (FIG. 17, EV and KRS). However, the effect of KRS on cell migration was diminished when laminin receptor was suppressed with its si-RNA (FIG. 17, si-LR, bottom panel). Since KRS is also secreted in some cancer cells as cytokine (Park, S. G. et al. Human lysyl-tRNA synthetase is secreted to trigger pro-inflammatory response, *Proc. Natl. Acad. Sci. USA* 102, 6356-6361 (2005)), the present inventors checked whether extracellular KRS would affect cell migration. When A549 cells were treated with purified KRS at different concentrations, cell migration was hardly affected, excluding the extracellular effect of KRS in this assay (FIG. 22). On the other hand, cellular protein synthesis and cell cycle were not influenced by suppression and over-expression of KRS during the period of experiments. This indicates that KRS-dependent cell migration did not result from its effect on these processes (FIGS. 23 and 24). Since laminin treatment results in the activation of MMP-2 (matrix metllo-proteinase-2) (Givant-Horwitz, V., Davidson, B. & Reich, R. Laminin-induced signaling in tumor cells the role of the M(r) 67,000 laminin receptor. *Cancer Res.* 64, 3572-3579 (2004)), they checked the role of KRS on the laminin-dependent activation of MMP-2 by using in vitro zymography assay. MMP-2 activity was enhanced by laminin, which was blocked in the presence of si-KRS (see the left side in FIG. 18), but further enhanced by over-expression of KRS (see the right side of FIG. 18).

Since KRS can facilitate cell migration via 67LR related to cancer metastasis, the inventors examined whether cancer metastasis would be affected by the expression level of KRS by using mouse mammary carcinoma 4T-1 cells that are highly metastatic to lungs. They suppressed the expression of either KRS or DRS (aspartyl-tRNA synthetase, another component of multi-ARS complex), with their specific siR-NAs, and compared how down-regulation of KRS and DRS would affect cancer metastasis. The inhibition effect of si-KRS and si-DRS was confirmed by western blotting (FIG. 25), and each of these cells and the cells treated with si-control was subcutaneously injected into the back skin of Balb/c mice. All of the three injected cells developed tumors of similar mass and volume (FIG. 26). This indicates that KRS level did not affect the growth of primary tumors. Lungs were isolated on day 21 after injection, and the numbers of the metastatic tumor nodules (larger than 1 mm in diameter) were compared between the 3 groups. The number of the metastatic nodules was significantly decreased by the suppression of KRS compared to those obtained from the control group and DRS-suppressed cells (FIGS. 19 and 27). Conversely, the inventors examined whether over-expression of KRS would enhance cancer metastasis by using the same method as described above. They firstly established 4T-1 cell lines stably over-expressing KRS by transfection of the KRS-encoding plasmid and G418 screening. In the established cell lines, KRS over-expression was confirmed by western blotting, and the inventors selected the two different cells (KRS-1 and KRS-2) expressing KRS at a higher amount than those transfected with empty vector (FIG. 28). These cells also generated primary tumors of similar mass and size (FIG. 29). When the inventors examined the lungs on day 30 after the injection of the cells, both of the KRS-over-expressing cells generated more nodules compared to those in the control group (FIGS. 20 and 30). This result indicates that KRS can induce cancer metastasis in vivo.

5. Determination on the Inhibition of the Interaction KRS and Laminin Receptor by the Compound of the Present Invention In order to determine if the compound of the present invention controls the interaction between KRS and laminin receptor, the present inventors determined the interaction between KRS and 67LR through treatment of the compound of the present invention. For this, the present inventors constructed a yeast two hybrid system in such a manner that cell growth can be caused by the interaction between KRS and laminin receptor, and then checked if the compound inhibits the interaction. If the compound inhibits the interaction between KRS and laminin receptor, the growth of yeast cells can be inhibited.

As a result, as noted in Table 2 below, the cells showed growth inhibition by about 50% as compared to that of a control group. Thus, it can be found that the compound can effectively inhibit the interaction between KRS and 67LR.

TABLE 2

| Compounds | Inhibition rate(%) |
|---|---|
| Compound of formula 2 | 54.22 |
| Compound of formula 3 | 59.98 |
| Compound of formula 4 | 51.78 |
| Compound of formula 5 | 47.55 |
| Compound of formula 6 | 52.79 |
| Compound of formula 7 | 47.63 |
| Compound of formula 8 | 47.28 |
| Compound of formula 9 | 36.88 |
| Compound of formula 10 | 60.04 |
| Compound of formula 11 | 49.09 |
| Compound of formula 12 | 52.46 |
| Compound of formula 13 | 55.22 |
| Compound of formula 14 | 49.27 |
| Compound of formula 15 | 52.10 |
| Compound of formula 16 | 47.56 |
| Compound of formula 17 | 36.49 |

Then, two different interaction pairs such as KRS-AIMP2 (Kim, J. Y. et al. p38 is essential for the assembly and stability of macromolecular tRNA synthetase complex: Implications for its physiological significance. *Proc. Natl. Acad. Sci. USA* 99, 7912-7916 (2002); Han, J. M. et al. Hierarchical network between the components of the multi-tRNA synthetase complex: Implications for complex formation. *J. Biol. Chem.* 281, 38663-38667 (2006)) and MRS-AIMP3 (Quevillon, S. & Mirande, M. The p18 component of the multisynthetase complex shares a protein motif with the beta and gamma subunits of eukaryotic elongation factor 1. *FEBS Lett.* 395, 63-67 (1996); Kim, K. J. et al. Determination of three dimensional structure and residues of novel tumor suppressor, AIMP3/p18, required for the interaction with ATM. *J. Biol. Chem.* (2008)) were treated with each compound. Through such a test, the present inventors selected a compound inhibiting only the KRS-LR interaction (see table 3 below).

TABLE 3

| | KRS-67LR | KRS-AIMP2 | MRS-AIMP3 |
|---|---|---|---|
| compound of formula 15 | 0.2223 | 0.9497 | 1.2443 |
| Control | 0.4241 | 1.3204 | 1.4732 |

From among the compounds, the inventors also examined whether the compound represented by Formula 15 (indicated by CAND-KL1, and KL1) can inhibit the intracellular interaction between KRS and 67LR. A549 cells were treated with KL1 at different concentrations. Then, 67LR was immunoprecipitated with its antibody, and co-immunoprecipitation of KRS was determined. The level of KRS co-precipitated with 67LR was decreased according the increase of KL1 level, and the intracellular levels of KRS and 67LR were not changed (FIG. 33). In vitro interaction between laminin receptor labeled with radioisotope and GST-KRS was carried out, and KL1 in different amounts was added thereto. The level of laminin receptor which has been subjected to pull-down with GST-KRS was decreased according to an increase of the added KL1 compound (FIG. 34). Since the intracellular stability of 67LR depends on the binding to KRS, it was determined if the treatment of KL1 inhibiting the binding between these two proteins affects the intracellular level of 67LR. The level of 67LR was decreased by the amount of added KL1, while the treatment had no effect on cytoplasmic 37LRP (FIG. 35). The present inventors examined whether KL1 is directly bound to KRS by using BIAcore 3000 through surface plasmon resonance. The binding of KL1 to KRS was increased according to an increase of the level of KL1, and Kd was measured to be about 2.6 µM (FIG. 36). It seems that KL1 is settled on the surface of KRS, while sterically inhibiting KRS from reaching laminin receptor.

6. Inhibition of KRS-67LR Inhibits Cell Migration and Cancer Metastasis.

Figure 37:
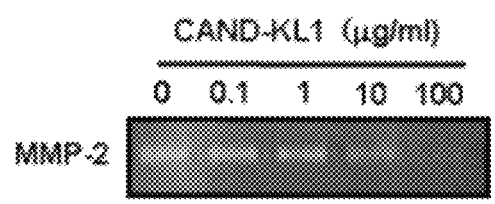
FIG. 37 shows the effect of the compound of the present invention on MMP2 activity.

The present inventors examined whether KL1 affects cell migration and cancer metastasis as above. In order to determine the effect on cell migration, the present inventors added KL1 in different amounts to MMP2 and transwell membrane assay. In the two assays, KL1 inhibited the MMP2 activity and the cell migration according to the treated amount (FIGS. 37 to 39). The intracellular protein synthesis and the viability were not influenced by KL1 treatment under the same experimental condition (FIGS. 40 and 41). This indicates that the inhibition of cell migration through compound treatment is not due to the protein synthesis and the cell viability. The present inventors performed an experiment of cancer metastasis in the presence or absence of KL1, in the same manner as described above. When KL1 was injected to mice for 3 weeks, in a dose of 30 mg/kg once a day, the number of metastasized nodules was significantly reduced (FIG. 42). On the other hand, KL1 did not affect the tumor growth (FIG. 43).

As can be seen foregoing, the present inventors confirmed that KRS has an effect on cancer metastasis by facilitating cancer (or tumor) cell migration through interaction with 67LR, and also found that a substance inhibiting the interaction between KRS and 67LR can prevent and treat cancer by inhibiting cancer cell metastasis. Accordingly, the composition of the present invention can inhibit cancer metastasis, and thus provide a novel means for prevention and treatment of cancer.

OTHER EMBODIMENTS

From the foregoing description, it will be apparent that variations and modifications may be made to the invention described herein to adopt it to various usages and conditions. Such embodiments are also within the scope of the following claims. The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof. All patents and publications mentioned in this specification are herein incorporated by reference to the same extent as if each independent patent and publication was specifically and individually indicated to be incorporated by reference.

The invention claimed is:

1. A method for inhibiting cancer metastasis, the method comprising administering to a subject in need of inhibiting cancer metastasis an effective amount of a benzo-heterocycle derivative of pharmaceutically acceptable salts thereof,
wherein benzo-heterocycle derivative is selected from the group consisting of N-(6-Methoxy-benzooxazol-2-yl)-benzamide of formula 2, N-(5-Methoxy-benzooxazol-2-yl)-benzamide of formula 3, (5-Chloro-benzooxazol-2-yl)-(3,4-dichloro-phenyl)-amine) of formula 6, N-Benzooxazol-2-yl-benzamide of formula 8, N-(5-Nitro-benzooxazol-2-yl)-benzamide of formula 9, N-(5-Methoxy-benzooxazol-2-yl)-benzamide of formula 10, N-(5-Methyl-benzooxazol-2-yl)-benzamide of formula 11, [2-(5-Methyl-benzooxazol-2-yl)-phenoxy]-acetic acid of formula 13, (2-(2,4,6-Trimethyl-phenyl)-benzooxazol-5-ylamine of formula 14, 2-[2-(4-Methyl-benzoylimino)-benzothiazol-3-yl]-butyric acid of formula 15, and (2-Chloro-4-fluoro-benzyl)-(5-fluoro-1H-indol-3-ylmethyl)-amine of formula 17,
wherein the cancer is selected from the group consisting of colon cancer, lung cancer, liver cancer, stomach cancer, esophagus cancer, pancreatic cancer, gall bladder cancer, kidney cancer, cervical cancer, endometrial carcinoma, choriocarcinoma, ovarian cancer, breast cancer, thyroid cancer, brain tumor, malignant melanoma, and lymphoma.

* * * * *